(12) United States Patent
Bossenmaier et al.

(10) Patent No.: US 7,179,812 B2
(45) Date of Patent: Feb. 20, 2007

(54) DIAZINE DERIVATIVES

(75) Inventors: Birgit Bossenmaier, Seefeld (DE); Walter-Gunar Friebe, Mannheim (DE); Wolfgang Jenni, Munich (DE); Matthias Rueth, Penzberg (DE); Edgar Voss, Bichl (DE)

(73) Assignee: Hoffmann-la Roche Inc., Nutley, NJ (US)

( * ) Notice: Subject to any disclaimer, the term of this patent is extended or adjusted under 35 U.S.C. 154(b) by 222 days.

(21) Appl. No.: 11/096,286

(22) Filed: Mar. 31, 2005

(65) Prior Publication Data

US 2005/0222228 A1 Oct. 6, 2005

(51) Int. Cl.
- C07D 413/14 (2006.01)
- A61K 31/497 (2006.01)
- A61K 31/501 (2006.01)
- A61K 31/506 (2006.01)

(52) U.S. Cl. ............ 514/252.05; 544/238; 544/316; 544/318; 544/319; 544/405; 514/255.05; 514/274

(58) Field of Classification Search ............ 544/238, 544/316, 318, 319, 405; 514/252.05, 255.05, 514/274
See application file for complete search history.

(56) References Cited

U.S. PATENT DOCUMENTS

2003/0069419 A1  4/2003  Ikemoto et al.

FOREIGN PATENT DOCUMENTS

| EP | 1270571 | 1/2003 |
|---|---|---|
| WO | WO 98/03505 | 1/1998 |
| WO | WO 01/77107 | 10/2001 |
| WO | WO 03/031442 | 4/2003 |
| WO | WO 03/059907 | 7/2003 |
| WO | WO 03/091247 | 11/2003 |

OTHER PUBLICATIONS

Wilks et al., Progress in Growth Factor Research, 2, pp. 97-111 (1990).
Chan et a., Cur. Opin. in Immunol., 8, pp. 394-401 (1995).
Yarden et al., Ann. Rev. Biochem., 57, pp. 443-478 (1988).
Wright et al., Br. J. Cancer, 65, pp. 118-121 (1992).
Baselga et al., Oncology, 63 (Suppl. 1), pp. 6-16 (2002).
Ranson et al., Oncology, 63 (Suppl. 1), pp. 17-24 (2002).
Bastin et al., Organic Proc. Res. Dev., 4, pp. 427-435 (2000).

*Primary Examiner*—Kansay Habte
(74) *Attorney, Agent, or Firm*—George W. Johnston; Patricia S. Rocha-Tramaloni; Brian C. Remy

(57) ABSTRACT

The present invention provides compounds of formula (I):

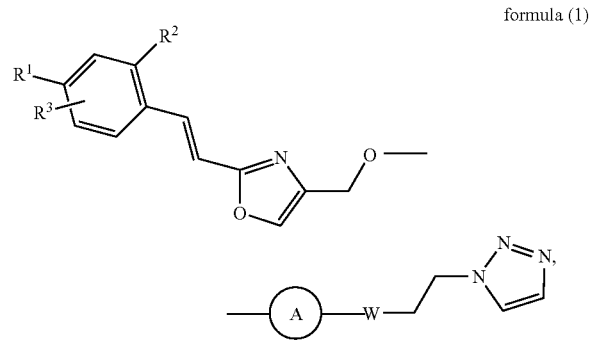

formula (1)

their pharmaceutically acceptable salts or esters, enantiomeric forms, diastereoisomers and racemates, the preparation of the above-mentioned compounds, pharmaceutical compositions containing them and their manufacture, as well as the use of the above-mentioned compounds in the control or prevention of illnesses such as cancer.

13 Claims, No Drawings

DIAZINE DERIVATIVES

PRIORITY TO RELATED APPLICATIONS

This application claims the benefit of European Application No. 04008130.9, filed Apr. 2, 2004, which is incorporated herein by reference in its entirety.

FIELD OF THE INVENTION

The present invention relates to novel diazine derivatives, to a process for their manufacture, pharmaceutical compositions containing them and their manufacture as well as the use of these compounds as pharmaceutically active agents for the prevention or treatment of cancer.

BACKGROUND OF THE INVENTION

Protein tyrosine kinases (PTKs) catalyse the phosphorylation of tyrosyl residues in various proteins involved in the regulation of cell growth and differentiation (Wilks et al., Progress in Growth Factor Research 97 (1990) 2; Chan, A. C., and Shaw, A. S., Curr. Opin. Immunol. 8 (1996) 394–401). Such PTKs can be divided into receptor tyrosine kinases (e.g. EGFR/HER-1, c-erB2/HER-2, c-met, PDGFr, FGFr) and non-receptor tyrosine kinases (e.g. src, lck). It is known that many oncogenes encode proteins which are aberrant tyrosine kinases capable of causing cell transformation (Yarden, Y., and Ullrich, A., Annu. Rev. Biochem. 57 (1988) 443–478; Larsen et al., Ann. Reports in Med. Chem., 1989, Chpt. 13). Also over-expression of a normal proto-oncogenic tyrosine kinase may result in proliferative disorders.

It is known that receptor tyrosine kinases of the HER-family like HER-2 and EGFR (HER-1) are frequently aberrantly expressed in common cancers such as breast cancer, gastrointestinal cancer such as colon, rectal or stomach cancer, leukemia and ovarian, bronchial and pancreatic cancer. High levels of these receptors correlate with poor prognosis and response to treatment (Wright, C., et al., Br. J. Cancer 65 (1992) 118–121).

Accordingly, it has been recognized that inhibitors of receptor tyrosine kinases are useful as selective inhibitors of the growth of mammalian cancer cells. Therefore several small molecule compounds as well as monoclonal antibodies are in clinical trials for the treatment of various types of cancer (Baselga, J., and Hammond, L. A., Oncology 63 (Suppl. 1) (2002) 6–16; Ranson, M., and Sliwkowski, M. X., Oncology 63 (suppl. 1) (2002) 17–24).

Some substituted oxazoles are known in the art. WO 98/03505, EP 1 270 571, WO 01/77107, WO 03/031442 and WO 03/059907 disclose related heterocyclic compounds as -tyrosine kinase inhibitors.

However, there remains a need for new compounds with improved therapeutic properties, such as enhanced activity, decreased toxicity, better solubility and improved pharmacokinetic profile, to name only a few.

SUMMARY OF THE INVENTION

The present invention relates to compounds of general formula I and pharmaceutically acceptable salts or esters thereof wherein formula I is:

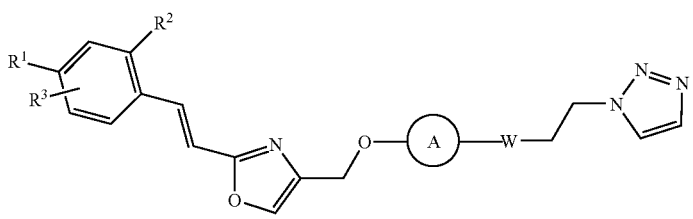

wherein:
(a) (1) $R^3$ is hydrogen and $R^1$ is selected from the group consisting of:
  (A) halogen;
  (B) —O-alkyl, wherein the alkyl group is optionally substituted with one or more halogens;
  (C) —S-alkyl, wherein the alkyl group is optionally substituted with one or more halogens;
  (D) —S(O)-alkyl, wherein the alkyl group is optionally substituted with one or more halogens;
  (E) —S(O)$_2$-alkyl, wherein the alkyl group is optionally substituted with one or more halogens;
  (F) —SF$_5$;
  (G) —NH-alkyl, wherein the alkyl group is optionally substituted with one or more halogens; and
  (H) alkyl, wherein the alkyl is optionally substituted with one or more halogens; or alternatively
(2) $R^1$ and $R^3$ are adjacent and together with the carbon atoms of the phenyl ring to which they are attached form a 5 or 6 membered heterocyclic ring;
(b) $R^2$ is selected from the group consisting of:
  (1) hydrogen; and
  (2) halogen;
(c) A is selected from the group consisting of:

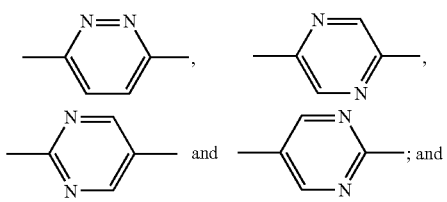

(d) W is selected from the group consisting of:
  (1) —CH$_2$—CH$_2$—;
  (2) —CH=CH—; and
  (3) —C≡C—.

The compounds of formula I are useful for preventing or treating proliferative diseases and conditions such as tumor growth and cancer including, but not limited to, breast cancer, leukemia, ovarian cancer, bronchial or lung cancer, pancreatic cancer, and gastrointestinal cancer such as colon cancer, rectal cancer, and stomach cancer.

The compounds of the present invention show activity as inhibitors of the HER-signalling pathway and therefore possess anti-proliferative activity. The present invention provides the compounds of formula I and their pharmaceutically acceptable salts or esters, enantiomeric forms, diastereoisomers and racemates, the preparation of the above-mentioned compounds, compositions containing them and their manufacture as well as the use of the above-mentioned compounds in the control or prevention of illnesses, especially of illnesses and disorders as mentioned above or in the manufacture of corresponding pharmaceutical compositions.

DETAILED DESCRIPTION OF THE INVENTION

As used herein, the term "alkyl" means a saturated, straight-chain or branched-chain hydrocarbon containing from 1 to 4, preferably from 1 to 2, carbon atoms, such as methyl, ethyl, n-propyl, isopropyl, n-butyl, 2-butyl, t-butyl. In addition, the present invention provides alkyl groups that may optionally be substituted with one or several halogen atoms, preferably fluorine. Examples are difluoromethyl, trifluoromethyl, 2,2,2-trifluoroethyl, perfluorethyl and the like.

As used herein, the term "halogen" denotes fluorine, chlorine, bromine and iodine, preferably fluorine and chlorine.

As used herein, the heterocyclic ring formed by $R^1$ and $R^3$ means a saturated or unsaturated hydrocarbon cycle with 5 or 6 ring atoms of which 1 or 2 atoms are replaced by heteroatoms selected from S, N or O, preferably selected from N or O; and the remaining carbon-atoms, where possible, are optionally once or several times substituted with halogen, preferably fluorine.

Preferably said "5 or 6 membered heterocyclic ring" is formed by $R^1$ and $R^3$ being located on two adjacent carbon-atoms of the phenyl ring to which they are attached. Examples of a "5 or 6 membered heterocyclic ring", including the phenyl ring to which it is attached, are benzo[1,3] dioxole, 2,2-difluoro-benzo[1,3]dioxole, 1H-benzimidazole, 2,3-dihydro-benzo[1,4]dioxin, 3,4-dihydro-2H-benzo[1,4] oxazine and the like.

As used herein the term "proliferative disease" means a cell proliferative disease including inflammatory diseases (e.g., rheumatoid arthritis) and oncological diseases such as, but not limited to, tumor growth and/or cancer including breast cancer, leukemia, ovarian cancer, bronchial or lung cancer, pancreatic cancer, and gastrointestinal cancer such as colon cancer, rectal cancer, and stomach cancer.

As used herein, when referring to the receptor tyrosine kinases of the HER-family like HER-2 and EGFR (HER-1), the acronym "HER" refers to human epidermal receptor and the acryonym "EGFR" refers to epidermal growth factor receptor.

As used herein, "THF" refers to tetrahydrofuran.

As used herein, the term "DMF" refers to N,N-dimethylformamide.

As used herein, the term "r.t." refers to room temperature.

As used herein, the term "EGTA" refers to Ethylene glycol-bis(2-aminoethylether)-N,N,N',N'-tetraacetic acid.

As used herein, the term "Hepes" refers to 4-(2-Hydroxyethyl)-1-piperazineethanesulfonic.

As used herein, the term "PMSF" refers to Phenylmethylsulfonyl fluoride.

As used herein, the term "Aprotinin" refers to a naturally occurring protein that is obtained and purified from cow's lungs.

As used herein, the term "Orthovanadate" refers to $Na_3VO_4$.

As used herein, the term "DMSO" refers to N,N-dimethylsulfoxide.

As used herein, the term "pY 1248" refers to the phosphorylated tyrosine residue 1248 of human epidermal receptor 2.

As used herein, "NSCLC cells" (e.g. QG56, A549, Calu-3) refers to Non-Small-Cell Lung Cancer cells.

As used herein, the term "NCI" refers to the National Cancer Institute.

As used herein, in relation to mass spectrometry (MS) the term "ESI+" refers to positive electrospray ionization mode.

As used herein, the term "$CDCl_3$" refers to deuterated chloroform.

As used herein, the term "Triton" refers to octyl phenol ethoxylate.

As used herein, the term "a therapeutically effective amount" of a compound means an amount of compound that is effective to prevent, alleviate or ameliorate symptoms of disease or prolong the survival of the subject being treated. Determination of a therapeutically effective amount is within the skill in the art.

The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 10 mg to about 10,000 mg, preferably from about 200 mg to about 1,000 mg, should be appropriate, although the upper limit may be exceeded when indicated. The daily dosage can be administered as a single dose or in divided doses, or for parenteral administration, it may be given as continuous infusion.

As used herein, a "pharmaceutically acceptable carrier" is intended to include any and all material compatible with pharmaceutical administration including solvents, dispersion media, coatings, antibacterial and antifungal agents, isotonic and absorption delaying agents, and other materials and compounds compatible with pharmaceutical administration. Except insofar as any conventional media or agent is incompatible with the active compound, use thereof in the compositions of the invention are contemplated. Supplementary active compounds can also be incorporated into the compositions.

The compounds according to the present invention may exist in the form of their pharmaceutically acceptable salts or esters. The term "pharmaceutically acceptable salt" refers to conventional acid-addition salts that retain the biological effectiveness and properties of the compounds of formula I and are formed from suitable non-toxic organic or inorganic acids. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, naphthalenesulfonic acid, naphthalenedisulfonic acid, methanesulfonic acid, ethanesulfonic acid, salicylic acid, oxalic acid, succinic acid, citric acid, malic acid, lactic acid, fumaric acid, and the like. The chemical modification of a pharmaceutical compound (i.e. a drug) into a salt is a technique well known to pharmaceutical chemists to obtain improved physical and chemical stability, hygroscopicity, flowability and solubility of compounds. See e.g. Bastin, R. J., et al, Organic Proc. Res. Dev. 4 (2000) 427–435.

Preferred are the pharmaceutically acceptable salts, which are formed with p-toluenesulfonic acid, naphthalenesulfonic acid, naphthalenedisulfonic acid, methanesulfonic acid and hydrochloric acid.

Preferred substituents in $R^1$ are trifluoromethyl, pentafluorosulfanyl, trifluoromethanesulfinyl, trifluoromethanesulfonyl, trifluoromethylsulfanyl, methoxy, difluoromethoxy, trifluoromethoxy, chloro and fluoro, especially trifluoromethyl, trifluoromethoxy and chloro.

When "$R^1$ and $R^3$ together with the carbon atoms to which they are attached form a 5 or 6 membered heterocyclic ring", the resulting bicyclic ring system, including the phenyl ring to which $R^1$ and $R^3$ are attached is preferably 2,2-difluorobenzo[1,3]dioxolyl.

A preferred embodiment of the invention are the compounds of formula I and pharmaceutically acceptable salts or esters thereof wherein:
  (a) $R^1$ is selected from the group consisting of:
    (1) halogen;
    (2) —O-alkyl, wherein the alkyl group is optionally substituted with one or more halogens;
    (3) —S-alkyl, wherein the alkyl group is optionally substituted with one or more halogens;
    (4) —S(O)-alkyl, wherein the alkyl group is optionally substituted with one or more halogens;
    (5) —S(O)$_2$-alkyl, wherein the alkyl group is optionally substituted with one or more halogens,
    (6) —SF$_5$,;
    (7) —NH-alkyl, wherein the alkyl group is optionally substituted with one or more halogens; and
    (8) alkyl, wherein the alkyl is optionally substituted with one or more halogens;
  (b) $R^2$ is selected from the group consisting of:
    (1) hydrogen; and
    (2) halogen;
  (c) $R^3$ is hydrogen;
  (d) A is selected from the group consisting of:

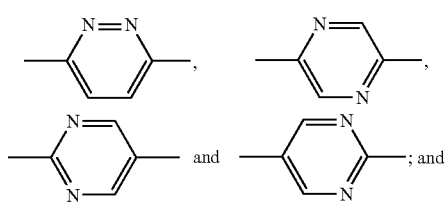

(e) W is selected from the group consisting of:
    (1) —CH$_2$—CH$_2$—;
    (2) —CH=CH—; and
    (3) —C≡C—.

In a more specific embodiment of the preceding preferred embodiment, A is:

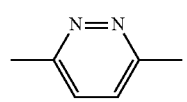

In another specific embodiment of the preceding preferred embodiment, A is:

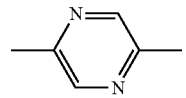

In an additional specific embodiment of the preceding preferred embodiment, A is:

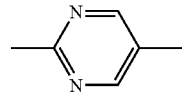

In a further particular embodiment of the above preferred embodiment, A is:

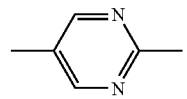

Another preferred embodiment are the compounds of formula I or pharmaceutically acceptable salts or esters thereof, wherein:
  (a) (1) $R^1$ and $R^3$ are adjacent and together with the phenyl ring to which they are attached form a 2,2-difluorobenzo[1,3]dioxolyl moiety, and $R^2$ is hydrogen; or alternatively,
      (2) $R^1$ is selected from the group consisting of:
        (A) fluorine;
        (B) chlorine;
        (C) —SF$_5$;
        (D) —O—CF$_3$;
        (E) —OCHF$_2$;
        (F) —S(O)—CF$_3$;
        (G) —S(O)$_2$—CF$_3$;
        (H) —S—CF$_3$; and
        (I) —CF$_3$;
      $R^2$ is selected from the group consisting of:
        (A) hydrogen;
        (B) fluorine; and
        (C) chlorine; and
      $R^3$ is hydrogen;
  (b) A is selected from the group consisting of:

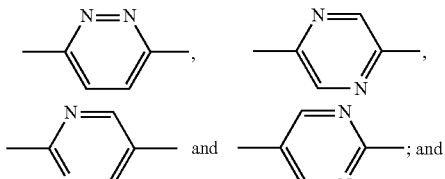

(c) W is selected from the group consisting of:
    (1) —CH$_2$—CH$_2$—;
    (2) —CH=CH—; and
    (3) —C≡C—.

In a more specific embodiment of the preceding preferred embodiment, A is:

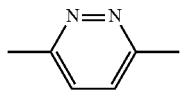

In another specific embodiment of the preceding preferred embodiment, A is:

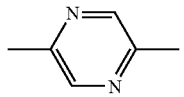

In an additional specific embodiment of the preceding preferred embodiment, A is:

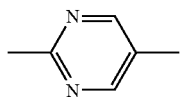

In a further particular embodiment of the above preferred embodiment, A is:

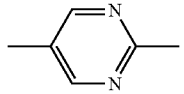

Another preferred embodiment are the compounds of formula I or pharmaceutically acceptable salts or esters thereof, wherein:
(a) $R^1$ is selected from the group consisting of:
  (1) chlorine;
  (2) —O—$CF_3$; and
  (3) —$CF_3$;
(b) $R^2$ is selected from the group consisting of:
  (1) hydrogen;
  (2) fluorine; and
  (3) chlorine;
(c) $R^3$ is hydrogen;
(d) A is selected from the group consisting of:

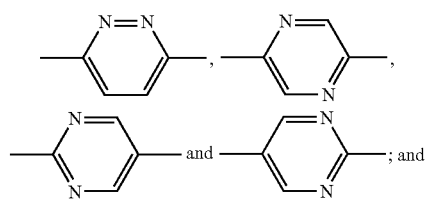

(e) W is selected from the group consisting of:
  (1) —$CH_2$—$CH_2$—;
  (2) —CH=CH—; and
  (3) —C≡C—.
In a more specific embodiment of the preceding preferred embodiment, A is:

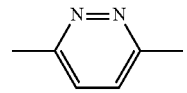

In another specific embodiment of the preceding preferred embodiment, A is:

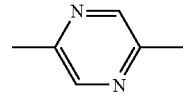

In an additional specific embodiment of the preceding preferred embodiment, A is:

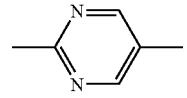

In a further particular embodiment of the above preferred embodiment, A is:

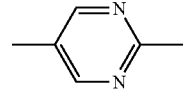

Still another preferred embodiment are the compounds of formula I or pharmaceutically acceptable salts or esters thereof, wherein:
(a) (1) $R^1$ and $R^3$ are adjacent and together with the phenyl ring to which they are attached form a 2,2-difluorobenzo[1,3]dioxolyl moiety, and $R^2$ is hydrogen; or alternatively,
  (2) $R^1$ is selected from the group consisting of:
    (A) fluorine;
    (B) chlorine;
    (C) —$SF_5$;
    (D) —O—$CF_3$;
    (E) —$OCHF_2$;
    (F) —S(O)—$CF_3$;
    (G) —$S(O)_2$—$CF_3$;
    (H) —S—$CF_3$; and
    (I) —$CF_3$;
  $R^2$ is selected from the group consisting of:
    (A) hydrogen;
    (B) fluorine; and
    (C) chlorine; and
  $R^3$ is hydrogen;
(b) A is:

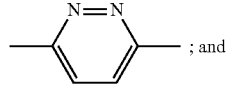

(c) W is selected from the group consisting of:
  (1) —$CH_2$—$CH_2$—;
  (2) —CH=CH—; and
  (3) —C≡C—.

Such compounds are for example:
3-(4-[1,2,3]Triazol-1-yl-but-1-ynyl)-6-{2-[2-(4-trifluoromethyl-phenyl)-vinyl]-oxazol-4-ylmethoxy}-pyridazine;
3-(4-[1,2,3]Triazol-1-yl-butyl)-6-{2-[2-(4-trifluoromethyl-phenyl)-vinyl]-oxazol-4-ylmethoxy}-pyridazine;
3-(4-[1,2,3]Triazol-1-yl-butyl)-6-{2-[(E)-2-(4-trifluoromethoxy-phenyl)-vinyl]-oxazol-4-ylmethoxy}-pyridazine;
3-{2-[(E)-2-(2-Fluoro-4-trifluoromethyl-phenyl)-vinyl]-oxazol-4-ylmethoxy}-6-(4-[1,2,3]-triazol-1-yl-butyl)-pyridazine; and
3-{2-[(E)-2-(4-Chloro-2-fluoro-phenyl)-vinyl]-oxazol-4-ylmethoxy}-6-(4-[1,2,3]triazol-1-yl-butyl)-pyridazine.

Another preferred embodiment are the compounds of formula I or pharmaceutically acceptable salts or esters thereof, wherein:
(a) $R^1$ is selected from the group consisting of:
   (1) chlorine;
   (2) —O—$CF_3$; and
   (3) —$CF_3$;
(b) $R^2$ is selected from the group consisting of:
   (1) hydrogen;
   (2) fluorine; and
   (3) chlorine;
(c) $R^3$ is hydrogen; and
(d) A is

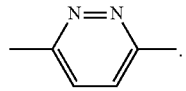

Yet another embodiment of the present invention are the compounds of formula I or pharmaceutically acceptable salts or esters thereof, wherein:
(a) (1) $R^1$ and $R^3$ are adjacent and together with the phenyl ring to which they are attached form a 2,2-difluoro-benzo[1,3]dioxolyl moiety, and $R^2$ is hydrogen; or alternatively,
(2) $R^1$ is selected from the group consisting of:
   (A) fluorine;
   (B) chlorine;
   (C) —$SF_5$;
   (D) —O—$CF_3$;
   (E) —$OCHF_2$;
   (F) —S(O)—$CF_3$;
   (G) —$S(O)_2$—$CF_3$;
   (H) —S—$CF_3$; and
   (I) —$CF_3$;
$R^2$ is selected from the group consisting of:
   (A) hydrogen;
   (B) fluorine; and
   (C) chlorine; and
$R^3$ is hydrogen;
(b) A is

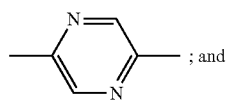; and (c) W is selected from the group consisting of:
   (1) —$CH_2$—$CH_2$—;
   (2) —CH=CH—; and
   (3) —C≡C—.

Such compounds are for example:
2-(4-[1,2,3]Triazol-1-yl-but-1-ynyl)-5-{2-[2-(4-trifluoromethyl-phenyl)-vinyl]-oxazol-4-ylmethoxy}-pyrazine;
2-(4-[1,2,3]Triazol-1-yl-butyl)-5-{2-[2-(4-trifluoromethyl-phenyl)-vinyl]-oxazol-4-ylmethoxy}-pyrazine; and
2-(4-[1,2,3]Triazol-1-yl-butyl)-5-{2-[(E)-2-(4-trifluoromethoxy-phenyl)-vinyl]oxazol-4-ylmethoxy}-pyrazine.

Another preferred embodiment are the compounds of formula I, wherein:
(a) $R^1$ is selected from the group consisting of:
   (1) chlorine;
   (2) —O—$CF_3$; and
   (3) —$CF_3$;
(b) $R^2$ is selected from the group consisting of:
   (1) hydrogen;
   (2) fluorine; and
   (3) chlorine;
(c) $R^3$ is hydrogen; and
(d) A is

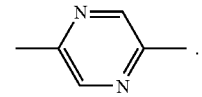

Yet another embodiment of the present invention are the compounds of formula I or pharmaceutically acceptable salts or esters thereof, wherein:
(a) (1) $R^1$ and $R^3$ are adjacent and together with the phenyl ring to which they are attached form a 2,2-difluoro-benzo[1,3]dioxolyl moiety, and $R^2$ is hydrogen; or alternatively,
(2) $R^1$ is selected from the group consisting of:
   (A) fluorine;
   (B) chlorine;
   (C) —$SF_5$;
   (D) —O—$CF_3$;
   (E) —$OCHF_2$;
   (F) —S(O)—$CF_3$;
   (G) —$S(O)_2$—$CF_3$;
   (H) —S—$CF_3$; and
   (I) —$CF_3$;
$R^2$ is selected from the group consisting of:
   (a) hydrogen;
   (b) fluorine;
   (c) chlorine; and
$R^3$ is hydrogen;
(b) A is

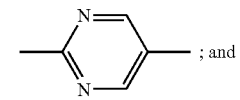; and (c) W is selected from the group consisting of:
   (1) —$CH_2$—$CH_2$—;
   (2) —CH=CH—; and
   (3) —C≡C—.

Such compounds are for example:
5-(4-[1,2,3]Triazol-1-yl-but-1-ynyl)-2-{2-[2-(4-trifluoromethyl-phenyl)-vinyl]-oxazol-4-ylmethoxy}-pyrimidine;

5-(4-[1,2,3]Triazol-1-yl-butyl)-2-{2-[2-(4-trifluoromethyl-phenyl)-vinyl]-oxazol-4-ylmethoxy}-pyrimidine;
5-(4-[1,2,3]Triazol-1-yl-butyl)-2-{2-[(E)-2-(4-trifluoromethoxy-phenyl)-vinyl]-oxazol-4-ylmethoxy}-pyrimidine;
2-{2-[(E)-2-(2-Fluoro-4-trifluoromethyl-phenyl)-vinyl]-oxazol-4-ylmethoxy}-5-(4-[1,2,3]-triazol-1-yl-butyl)-pyrimidine; and
2-{2-[(E)-2-(4-Chloro-2-fluoro-phenyl)-vinyl]-oxazol-4-ylmethoxy}-5-(4-[1,2,3]triazol-1-yl-butyl)-pyrimidine.

Another preferred embodiment are the compounds of formula I, wherein:
(a) $R^1$ is selected from the group consisting of:
  (1) chlorine;
  (2) —O—$CF_3$; and
  (3) —$CF_3$;
(b) $R^2$ is selected from the group consisting of
  (1) hydrogen;
  (2) fluorine; and
  (3) chlorine;
(c) $R^3$ is hydrogen; and
(d) A is

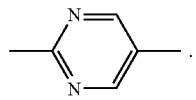

Another embodiment of the present invention are the compounds of formula I or pharmaceutically acceptable salts or esters thereof, wherein:
(a) (1) $R^1$ and $R^3$ are adjacent and together with the phenyl ring to which they are attached form a 2,2-difluoro-benzo[1,3]dioxolyl moiety, and $R^2$ is hydrogen; or alternatively,
  (2) $R^1$ is selected from the group consisting of:
    (A) fluorine;
    (B) chlorine;
    (C) —$SF_5$;
    (D) —O—$CF_3$;
    (E) —$OCHF_2$;
    (F) —S(O)—$CF_3$;
    (G) —$S(O)_2$—$CF_3$;
    (H) —S—$CF_3$; and
    (I) —$CF_3$;
  $R^2$ is selected from the group consisting of:
    (A) hydrogen;
    (B) fluorine; and
    (C) chlorine; and
  $R^3$ is hydrogen;
(b) A is

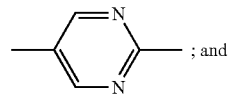
; and (c) W is selected from the group consisting of:
  (1) —$CH_2$—$CH_2$—;
  (2) —CH=CH—; and
  (3) —C≡C—.

Such a compound is for example:
2-(4-[1,2,3]Triazol-1-yl-butyl)-5-{2-[2-(4-trifluoromethyl-phenyl)-vinyl]-oxazol-4-ylmethoxy}-pyrimidine Another preferred embodiment are the compounds of formula I, wherein:
(a) $R^1$ is selected from the group consisting of:
  (1) chlorine;
  (2) —O—$CF_3$; and
  (3) —$CF_3$;
(b) $R^2$ is selected from the group consisting of:
  (1) hydrogen;
  (2) fluorine; and
  (3) chlorine;
(c) $R^3$ is hydrogen; and
(d) A is

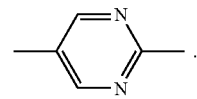

Still another embodiment of the invention is a process for the manufacture of the compounds of formula (I), wherein:
(a) the compound of formula (XII)

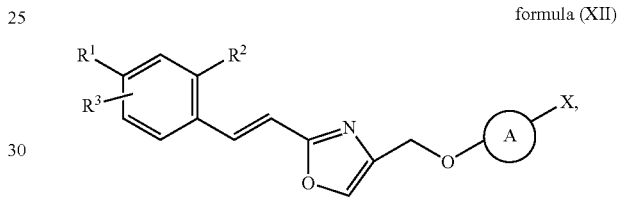

wherein A is

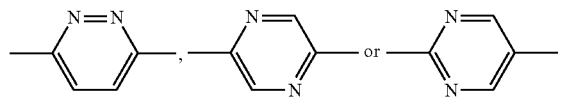

and X is bromine or iodine is reacted with but-3-ynyl-1H-[1,2,3]triazole, shown below:

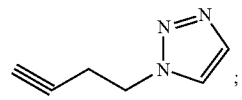

(b) if desired, the compound of formula (I) (wherein W is —C≡C—) obtained in (a), is further reacted in a reductive step to give the corresponding compound of formula (I) wherein W is —$CH_2$—$CH_2$— or —CH=CH— or;
(c) said compound of formula (I) is isolated from the reaction mixture, and
(d) if desired, converted into a pharmaceutically acceptable salt.

The diazine derivatives of the general formula (I), or a pharmaceutically acceptable salt or ester thereof, may be prepared by any process known to be applicable for the preparation of chemically-related compounds by the one skilled in the art. Such processes, when used to prepare the diazine derivatives of formula (I), or a pharmaceutically-acceptable salt or ester thereof, are provided as a further feature of the invention and are illustrated by the following representative examples of scheme 1 to scheme 4, in which, unless otherwise stated, $R^1$, $R^2$, $R^3$, A and W have the significance given herein before. Necessary starting materials are commercially available or may be obtained by standard procedures of organic chemistry. The preparation of such starting materials is described within the accompanying non-limiting examples, in U.S. Ser. No. 03/069419 or WO 03/091247. Alternatively necessary starting materials are obtainable by analogous procedures to those illustrated which are within the ordinary skill of an organic chemist.

The manufacture of the compounds of formula (I) varies according to the nature of "A" in formula (I). The compounds of the present invention wherein "A" is pyridazine can be prepared according to scheme 1, and are named (Ia).

like tetrahydrofuran, dichloromethane, N,N-dimethylformamide and mixtures thereof at temperatures varying from −30° C. to 40° C. The addition of ammonia yields the amides of formula (IV).

With step 3, scheme 1 the chlorides of formula (V) are synthesized using commonly known methods. The amides of formula (IV) and 1,3-dichloroacetone are subjected to a condensation/dehydration sequence yielding the compounds of formula (V). Typical solvents for reactions of this kind are toluene, benzene, acetone and chloroform. If desired the reaction can be carried out under solvent free conditions. The reaction temperatures may vary from 50° C. to 150° C.

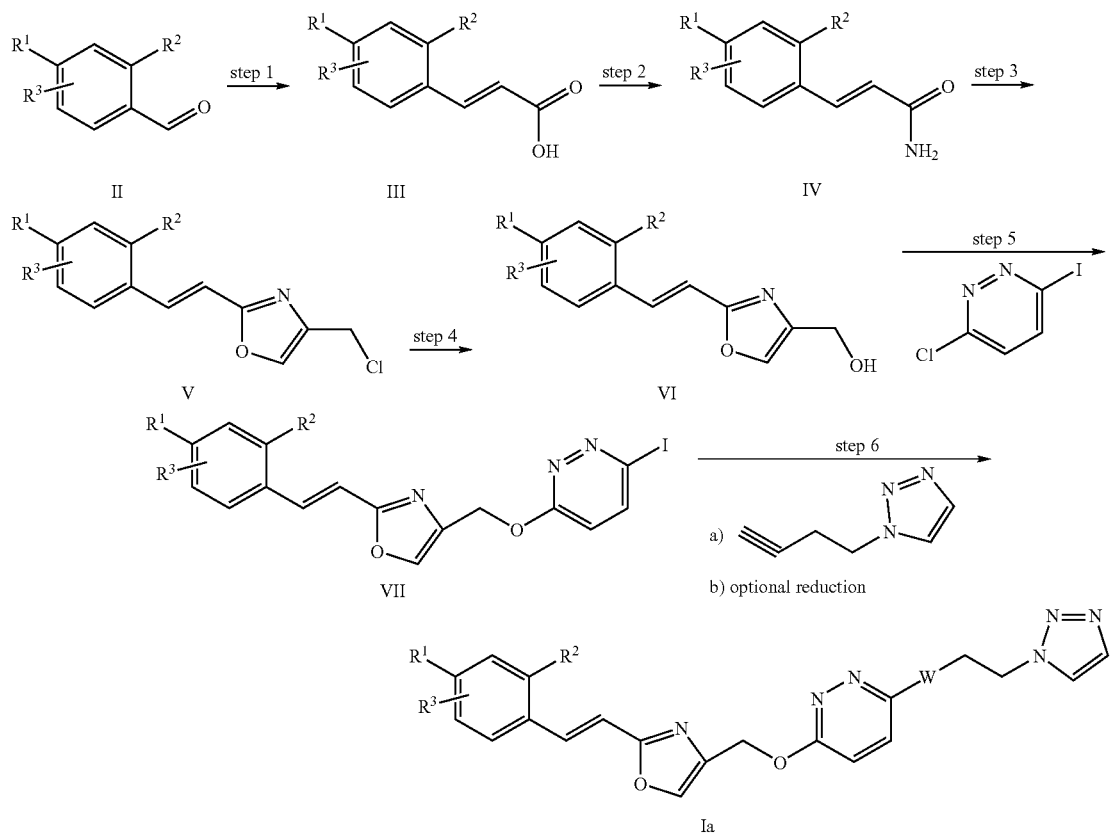

Scheme 1

A preferred method for the synthesis of the compounds of formula (Ia) starts from the corresponding benzaldehydes of formula (II), wherein $R^1$, $R^2$ and $R^3$ have the significance as given above for formula I. Step 1 of the reaction sequence (scheme 1) is a Knoevenagel condensation with malonic acid and concomitant decarboxylation, yielding the acrylic acid derivatives of formula (III). The reaction is typically carried out in solvents like pyridine, N-methylpyrrolidinone, acetonitrile, N,N-dimethylformamide and mixtures thereof at temperatures up to 140° C. or under reflux. Typically used bases are piperidine, triethylamine and diisopropylamine.

In step 2, scheme 1 the obtained compounds of formula (III) are converted into their corresponding amides of formula (IV), using methods well known to someone skilled in the art, e.g. by activating the carboxylic group in said compounds of formula (III) with oxalyl chloride in solvents In step 4, scheme 1 the hydroxymethyl oxazole derivatives of formula (VI) are obtained. This reaction is typically performed in a two step procedure, starting with the reaction of the chlorides of formula (V) with sodium or potassium acetate which is typically performed in solvents like N,N-dimethylformamide, N-methylpyrrolidinone, acetonitrile, dimethylsulfoxide and mixtures thereof at temperatures between 50° C. and 140° C. or at reflux. In the second step hydrolysis of the resulting acetates is achieved by standard methods for someone skilled in the art. Typically used bases are e.g. sodium hydroxide (NaOH), potassium hydroxide (KOH) or lithium hydroxide (LiOH) in solvents like water, tetrahydrofuran, N,N-dimethylformamide, dimethylsulfoxide, methanol, ethanol or mixtures thereof at temperatures between 0° C. and 150° C., yielding the hydroxymethyl derivatives of formula (VI).

Step 5 scheme 1 is an addition-elimination reaction of the hydroxymethyl derivatives of formula (VI) and 3-chloro-6-iodopyridazine which is typically performed in solvents like tetrahydrofuran, acetonitrile, N,N-dimethylformamide and mixtures thereof at temperatures between −20° C. and 50° C., yielding the iodo-pyridazines of formula (VII). The reaction is carried out in the presence of a non nucleophilic base like sodium tert-butoxide, potassium tert-butoxide, N-ethyl-N,N-diisopropyl amine, triethyl amine or the like. Alternatively the reaction could be carried out with 3,6-diiodo-pyridazine instead of 3-chloro-6-iodopyridazine under analogous reaction conditions.

tetrahydrofuran, acetone, ethyl acetate or mixtures thereof. Alternatively sodium metal in liquid ammonia is used to hydrogenate the alkyne group (W is —C≡C—) to an alkene group (W is —HC═CH—).

Alternatively, the steps 5 and 6 in scheme 1 can be carried out in reverse order to yield the products of formula (Ia).

A preferred method for the synthesis of the derivatives of formula (I), wherein A is a pyrimidine which is linked via the oxygen atom at the 2-position and the W group at the 5-position is described in scheme 2. The derivatives of formula (I), wherein A represents such a pyrimidine are named Ib in scheme 2.

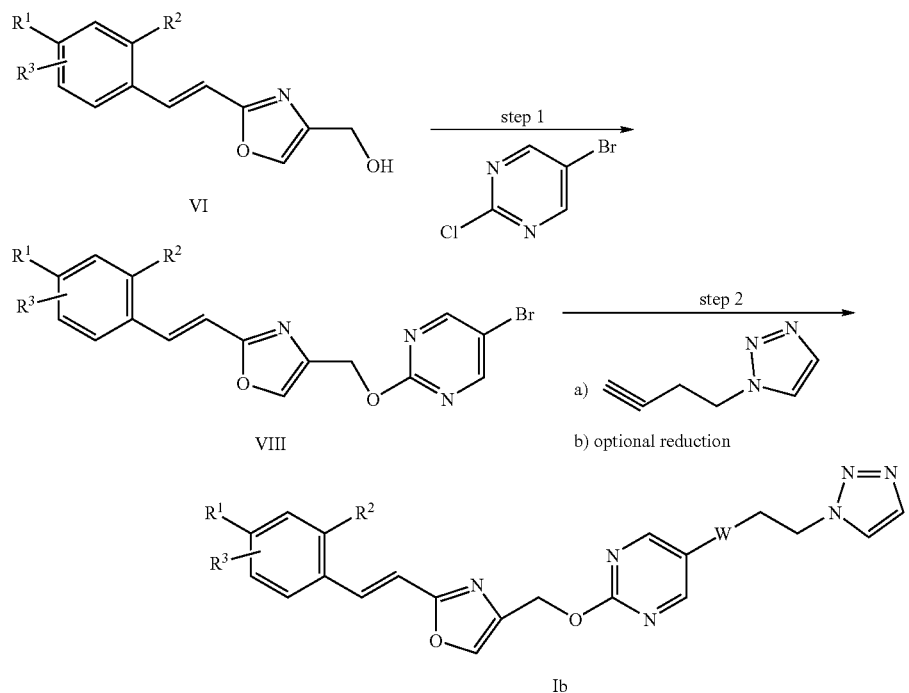

In step 6, scheme 1 the obtained iodo-pyridazines of formula (VII) are reacted with 1-But-3-ynyl-1H-[1,2,3]triazole in a Sonogashira cross-coupling reaction in the presence of catalytic amounts of copper iodide and a palladium complex, e.g. Pd(PPh$_3$)$_4$, Pd(PPh$_3$)$_2$Cl$_2$ or the like. The reaction is carried out in the presence of a base like triethyl amine, diisopropyl amine, isopropyl amine, piperidine, morpholine or pyrrolidine and in solvents like tetrahydrofuran, N,N-dimethylformamide or mixtures thereof at temperatures varying from 20° C. to 100° C. yielding derivatives of formula (Ia) wherein W is —C≡C— (reaction a), step 6).

When the synthesis is further proceeded by the reduction step b) in step 6 the compounds of formula (Ia) wherein W is —HC═CH— or —CH$_2$—CH$_2$— are obtained. Preferably, as reduction reaction a catalytic hydrogenation is performed using different catalytic species like Lindlar catalysts or certain nickel borides (to obtain compounds wherein W is —HC═CH—), palladium on activated charcoal, nickel or platinum (to obtain compounds wherein W is —CH$_2$—CH$_2$—). The reaction is typically carried out at temperatures between 0° C. and 50° C., at hydrogen pressures between 1 to 4 atm in solvents like methanol, ethanol, Starting materials are the corresponding hydroxymethyl derivatives of formula (VI) scheme 1, wherein R$^1$, R$^2$ and R$^3$ have the meaning given herein before. Step 1 scheme 2 of the reaction sequence is an addition-elimination reaction of the hydroxymethyl derivatives of formula (VI) and 5-bromo-2-chloro-pyrimidine which is typically performed in solvents like tetrahydrofuran, acetonitrile, N,N-dimethylformamide and mixtures thereof at temperatures between 0° C. and 50° C., yielding the bromo-pyrimidines of formula (VIII). The reaction is carried out in the presence of a non nucleophilic base like sodium tert-butoxide, potassium tert-butoxide, N-ethyl-N,N-diisopropyl amine, triethyl amine or the like.

In step 2, scheme 2 the bromo-pyrimidines of formula (VIII) are reacted with 1-but-3-ynyl-1H-[1,2,3]triazole in a Sonogashira cross-coupling reaction in the presence of catalytic amounts of copper iodide and a palladium complex, e.g. Pd(PPh$_3$)$_4$, Pd(PPh$_3$)$_2$Cl$_2$ or the like. The reaction is carried out in the presence of a base like triethyl amine, diisopropyl amine, isopropyl amine, piperidine, morpholine or pyrrolidine and in solvents like tetrahydrofuran, N,N-dimethylformamide or mixtures thereof at temperatures varying from 20° C. to 100° C. yielding derivatives of formula (Ib) wherein W is —C≡C— (reaction a), step 2).

Further proceeding the reaction by the reduction reaction b) in step 2 yields the compounds of formula (Ib) wherein W is —HC=CH— or —CH$_2$—CH$_2$—. A preferred reduction reaction b) in step 2 is a catalytic hydrogenation which is carried out using different catalytic species like Lindlar catalysts or certain nickel borides (to obtain compounds wherein W is —HC=CH—), palladium on activated charcoal, nickel or platinum (to obtain compounds wherein W is —CH$_2$—CH$_2$—). The reaction is typically performed at temperatures between 0° C. and 50° C., at hydrogen pressures between 1 to 4 atm in solvents like methanol, ethanol, tetrahydrofuran, acetone, ethyl acetate or mixtures thereof. Alternatively sodium metal in liquid ammonia is used to hydrogenate the alkyne group (W is —C≡C—) to an alkene group (W is —HC=CH—).

Alternatively, the steps 1 and 2 in scheme 2 can be carried out in reverse order to yield the products of formula (Ib).

The synthesis of the derivatives of formula (I), wherein A is a pyrimidine which is linked via the oxygen atom at the 5-position and the W group at the 2-position is described in scheme 3. The derivatives of formula (I), wherein A represents such a pyrimidine are named Ic in scheme 3.

peratures varying from 20° C. to 80° C. yielding the compounds of formula (IX) wherein W is —C≡C— (reaction a), step 1).

Further proceeding the reaction by the reduction reaction b) in step 1 scheme 3 yields the compounds of formula (IX) wherein W is —HC=CH— or —CH$_2$—CH$_2$—. A preferred reduction reaction b) in step 1 is the catalytic hydrogenation using different catalytic species like Lindlar catalysts or certain nickel borides (to obtain compounds wherein W is —HC=CH—), palladium on activated charcoal, nickel or platinum (to obtain compounds wherein W is —CH$_2$—CH$_2$—). The reaction is typically performed at temperatures between 0° C. and 50° C. and at hydrogen pressures between 1 to 4 atm in solvents like methanol, ethanol, tetrahydrofuran, acetone, ethyl acetate or mixtures thereof. Alternatively sodium metal in liquid ammonia is used to hydrogenate the alkyne group (W is —C≡C—) to an alkene group (W is —HC=CH—).

In step 2, scheme 3 the pyrimidin-5-ol derivatives of formula (X) are obtained. This reaction is typically performed in a two step procedure, starting with the reaction of the compounds of formula (IX) with bis(pinacolato)diboron in the presence of catalytic amounts of a palladium complex like dichloro[1,1'-bis-(diphenylphosphino)ferrocene] palla-

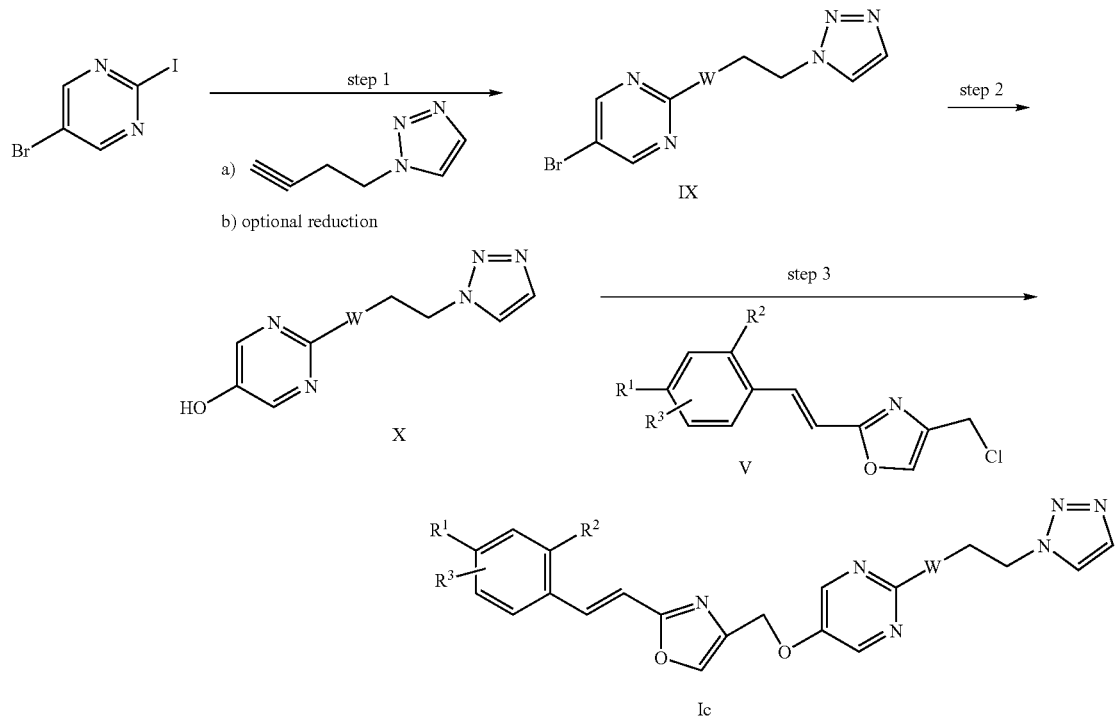

Scheme 3

In step 1, scheme 3 of the reaction sequence 5-bromo-2-iodo-pyrimidine is reacted with 1-but-3-ynyl-1H-[1,2,3]triazole in a Sonogashira cross-coupling reaction in the presence of catalytic amounts of copper iodide and a palladium complex, e.g. Pd(PPh$_3$)$_4$, Pd(PPh$_3$)$_2$Cl$_2$ or the like. The reaction is carried out in the presence of a base like triethyl amine or diisopropyl amine and in solvents like tetrahydrofuran, N,N-dimethyl-formamide or mixtures thereof at temdium (II) (PdCl2(dppf)), bis(dibenzylidene-acetone)-palladium (Pd(dba)$_2$), tris(dibenzylideneacetone)-dipalladium (Pd$_2$(dba)$_3$) or palladium acetate (Pd(OAc)2) and optionally various phosphine or imidazolium ligands e.g. tricyclohexylphosphine, 2-dicyclohexylphosphino-2'-(N,N-dimethylamino)biphenyl, 1-butyl-3-methyl-1H-imidazolium tetrafluoroborate, 1,3-bis(2,6-diisopropylphenyl)-1H-imidazolium chloride. The reaction is typically performed in solvents like dimethylsulfoxide, dioxane, tetrahydrofuran, N,N-dimethyl-formamide, acetonitrile, 1,2-dimethoxyethane and mixtures thereof at temperatures between 50° C. and 140° C. or at reflux in the presence of bases like potassium acetate, potassium phosphate or potassium carbonate. Alternatively the resulting boronic acid derivatives are obtained using n-butyllithium and various organic borates like triisopropylborate or trimethylborate or the like at temperatures between −100° C. and 30° C. in solvents like toluene, hexane and tetrahydrofuran and mixtures thereof. In the second step the oxidation of the resulting boronic acid derivatives is achieved by standard methods for someone skilled in the art. Typically used oxidation reagents are e.g. hydrogen peroxide or potassium peroxymonosulfate (2KHSO5 KHSO4 K2SO4) in solvents like water, tetrahydrofuran, acetone or mixtures thereof at temperatures between 0° C. and 80° C., yielding the pyrimidin-5-ol derivatives of formula (X).

The derivatives of formula (Ic) can be obtained by reactions well known to someone skilled in the art, e.g. by alkylation of pyrimidin-5-ol derivatives of formula (X) with the chlorides of formula (V), wherein $R^1$, $R^2$ and $R^3$ have the significance as given above for formula I, according to reaction step 3 scheme 3. Typically the alkylation is carried out in solvents like N,N-dimethyl formamide or acetonitrile. Typical bases for this reaction are sodium carbonate, potassium carbonate, cesium carbonate, sodium methylate, sodium hydride, lithium diisopropyl amide. The reaction temperatures may vary from 50° C. to 150° C.

The compounds of the present invention, wherein "A" is pyrazine, can be prepared according to scheme 4, and are named (Id).

Starting materials are the corresponding the chlorides of formula (V) scheme 1, wherein $R^1$, $R^2$ and $R^3$ have the meaning given herein before. The oxazole derivatives of formula (XI) can be obtained by reactions well known to someone skilled in the art, e.g. by O-alkylation of 5-bromo-pyrazin-2-ol with said chlorides of formula (V), wherein $R^1$, $R^2$ and $R^3$ have the significance as given above for formula I, according to reaction step 1 scheme 4. Typically the alkylation is carried out in solvents like N,N-dimethyl formamide or acetonitrile. Typical bases for this reaction are sodium carbonate, potassium carbonate, cesium carbonate, sodium methylate, sodium hydride, lithium diisopropylamide. The reaction temperatures may vary from 50° C. to 150° C.

In step 2, scheme 4 the bromo-pyrazines of formula (VIII) are reacted with 1-but-3-ynyl-1H-[1,2,3]triazole in a Sonogashira cross-coupling reaction in the presence of catalytic amounts of copper iodide and a palladium complex, e.g. $Pd(PPh_3)_4$, $Pd(PPh_3)_2Cl_2$ or the like. The reaction is carried out in the presence of a base like triethyl amine, diisopropyl amine, isopropyl amine, piperidine, morpholine or pyrrolidine and in solvents like tetrahydrofuran, N,N-dimethylformamide or mixtures thereof at temperatures varying from 20° C. to 120° C. yielding derivatives of formula (Id) wherein W is —C≡C— (reaction a), step 2).

Further proceeding the reaction by the reduction reaction b) in step 2 yields the compounds of formula (Id) wherein W is —HC═CH— or —$CH_2$—$CH_2$—. A preferred reduction reaction b) in step 2 is a catalytic hydrogenation which is carried out using different catalytic species like Lindlar catalysts or certain nickel borides (to obtain compounds wherein W is —HC═CH—), palladium on activated charcoal, nickel or platinum (to obtain compounds wherein W is —$CH_2$—$CH_2$—). The reaction is typically performed at temperatures between 0° C. and 50° C., at hydrogen pressures between 1 to 4 atm in solvents like methanol, ethanol, tetrahydrofuran, acetone, ethyl acetate or mixtures thereof. Alternatively sodium metal in liquid ammonia is used to hydrogenate the alkyne group (W is —C≡C—) to an alkene group (W is —HC═CH—).

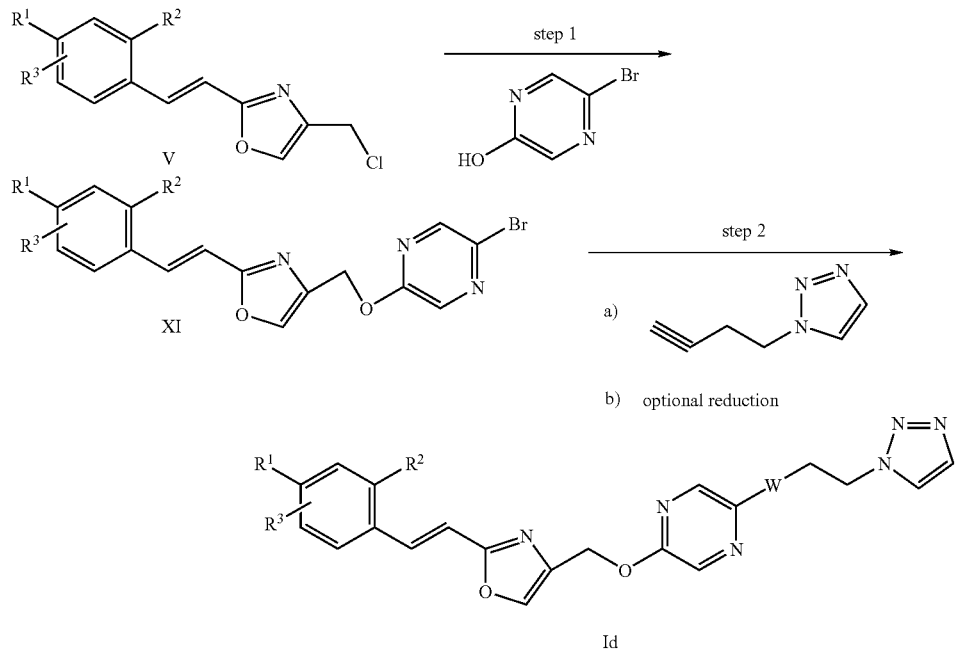

Alternatively the pyrazine derivatives of the formula (Id), can be prepared according to scheme 5.

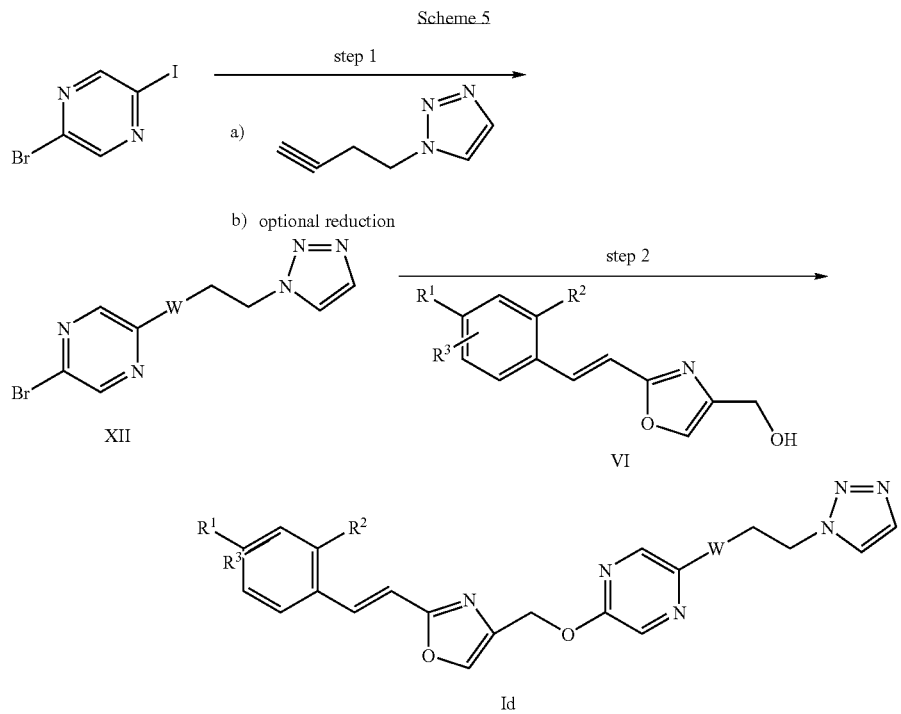

Scheme 5

In scheme 5 the W, R¹, R² and R¹ have the significance given above. The synthesis of the compounds of formula Id in scheme 5 starts from the corresponding 5-bromo-2-iodo-pyrazine, which can prepared from 5-amino-2-iodo-pyrazole according to WO 2004/000811.

In step 1, scheme 5 the 5-bromo-2-iodo-pyrazine is reacted with 1-but-3-ynyl-1H-[1,2,3]triazole in a Sonogashira cross-coupling reaction in the presence of catalytic amounts of copper iodide and a palladium complex, e.g. Pd(PPh$_3$)$_4$, Pd(PPh$_3$)$_2$Cl$_2$ or the like. The reaction is carried out in the presence of a base like triethyl amine, diisopropyl amine, isopropyl amine, piperidine, morpholine or pyrrolidine and in solvents like tetrahydrofuran, N,N-dimethylformamide or mixtures thereof at temperatures varying from 20° C. to 120° C. yielding bromo-pyrazine derivatives of formula (XII) wherein W is —C≡C— (reaction a), step 1).

Further proceeding the reaction by the reduction reaction b) in step 1 yields the compounds of formula (XII) wherein W is —HC═CH— or —CH$_2$—CH$_2$—. A preferred reduction reaction b) in step 2 is a catalytic hydrogenation which is carried out using different catalytic species like Lindlar catalysts or certain nickel borides (to obtain compounds wherein W is —HC═CH—), palladium on activated charcoal, nickel, platinum or platinum(IV) oxide (to obtain compounds wherein W is —CH$_2$—CH$_2$—). The reaction is typically performed at temperatures between 0° C. and 50° C., at hydrogen pressures between 1 to 4 atm in solvents like methanol, ethanol, tetrahydrofuran, acetone, ethyl acetate or mixtures thereof. Alternatively sodium metal in liquid ammonia is used to hydrogenate the alkyne group (W is —C≡C—) to an alkene group (W is —HC═CH—).

Step 2 scheme 5 of the reaction sequence is an addition-elimination reaction of the hydroxymethyl derivatives of formula (VI) and bromo-pyrazine derivatives of Formula (XII), which is typically performed in solvents like tetrahydrofuran, acetonitrile, N,N-dimethylformamide and mixtures thereof at temperatures between 0° C. and 50° C., yielding the compounds of formula (Id). The reaction is carried out in the presence of a non nucleophilic base like sodium tert-butoxide, potassium tert-butoxide, N-ethyl-N, N-diisopropyl amine, triethyl amine or the like.

Compounds of formulas VII, VIII, IX, X, XI and XII are new and also subject of this invention. The compounds of formula I can contain one or several chiral centers and can then be present in a racemic or in an optically active form. The racemates can be separated according to known methods into the enantiomers. For instance, diastereomeric salts which can be separated by crystallization are formed from the racemic mixtures by reaction with an optically active acid such as e.g. D- or L-tartaric acid, mandelic acid, malic acid, lactic acid or camphorsulfonic acid. Alternatively separation of the enantiomers can also be achieved by using chromatography on chiral HPLC-phases which are commercially available.

The compounds of formula (I) and their pharmaceutically acceptable salts or esters possess valuable pharmacological properties. It has been found that said compounds inhibit the HER-signaling pathway and show anti-proliferative activity. Consequently the compounds of the present invention are useful in the therapy and/or prevention of illnesses with known over-expression of receptor tyrosine kinases of the HER-family like HER-2 and EGFR (HER-1), especially in the therapy and/or prevention of illnesses mentioned above. The activity of the present compounds as HER-signaling pathway inhibitors is demonstrated by the following biological assay:

Inhibition of HER2 Phosphorylation in Calu3 Tumor Cell Line $2\times10^5$ Calu3 cells per well were plated in a 12-well plate. After 4 days cells were starved for 16 h in DMEM(Dulbecco's Modified Eagle Medium)/0.5% FCS(Fetal Calf Serum)/1% Glutamine. During this time cells were incubated with 1 µM of the compound. Afterwards cells were lysed in lyses buffer containing 1% Triton, 10% Glycerol, 1 mM EGTA, 1.5 mM $MgCl_2$, 150 mM NaCl, 50 mM Hepes pH 7.5, 1 mM PMSF, 10 µg/mL Aprotinin and 0.4 mm Orthovanadate. Cell lysates were analyzed on a SDS PAGE and after transfer to a nitrocellulose membrane detected with an antibody specifically recognizing the pY 1248 in HER2. Inhibition of HER2 phosphorylation is calculated as percentage of the DMSO treated control. This percentage is calculated according to the following formula: Inhibition in %=100−(Phosphorylated-HER2-Signal of Test Sample*100/Phosphorylated-HER2-Signal DMSO-control).

With all compounds, a significant inhibition of HER2-phosphorylation was detected, which is exemplified by the compounds shown in Table 1. The reference compound as used herein is 1-[4-(4-{2-[2-(4-trifluoromethyl-phenyl)-vinyl]-oxazol-4-ylmethoxy}-phenyl)-butyl]-1H-[1,2,3]triazole (Example 4, p. 88, WO 01/77107).

TABLE 1

|  | Control (DMSO) | Percent inhibition of HER2-phosphorylation (compound concentration 1 µM) |
|---|---|---|
| reference compound | 0 | 52.3 |
| example 2 | 0 | 79.8 |
| example 4 | 0 | 72.7 |
| example 7 | 0 | 75.3 |

In Vivo Assay on Tumor Inhibition:

To generate primary tumors, NSCLC (e.g. QG56, A549, Calu-3) cells ($4–5.0\times10^6$ in a volume of 100 µl) are injected subcutaneously into the left flank of female SCID beige mice (severe combined immunodeficient/beige mice available from Charles River, Sulzfeld, Deutschland) or BALB/c nude mice (BALB/c nude spontaneous mutant mice [homozygotes] available from Taconic Europe [former M&B A/S (Mollegaard and Bomholtgard Breeding and Research Centre] in Denmark) using a 1 ml syringe and a 26 G needle. The tumor cells are originally obtained from the NCI and deposited in a working cell bank. The cells are thawed and expanded in vitro before use in the experiment. Mice are assigned to the treatment groups 14–21 days after cell injection. For grouping (n=10–15 mice per group), the animals are randomized to get a similar mean primary tumor volume of ca. 100–150 $mm^3$ per group. The test compounds are administered orally once per day as a suspension in 7.5% gelatine 0.22% NaCl with an administration volume of 10 ml/kg based on actual body weights. Treatment is initiated one day after staging, and carried out until day 20–50, the final day of the study. The subcutaneous primary tumors are measured twice weekly, starting prior to randomisation, in two dimensions (length and width) using an electronic caliper. The volume of the primary tumor is calculated using the formula: $V[mm^3]=(length\ [mm]\times width\ [mm]\times width\ [mm])/2$. In addition, the body weight of all animals is recorded at least twice weekly. Finally, at the end of the study the tumors are explanted and weighed.

The compounds according to this invention and their pharmaceutically acceptable salts or esters can be used as medicaments, e.g. in the form of pharmaceutical compositions. The pharmaceutical compositions can be administered orally, e.g. in the form of tablets, coated tablets, dragées, hard and soft gelatine capsules, solutions, emulsions or suspensions. The administration can, however, also be effected rectally, e.g. in the form of suppositories, or parenterally, e.g. in the form of injection solutions.

The above-mentioned pharmaceutical compositions can be obtained by processing the compounds according to this invention with pharmaceutically inert, inorganic or organic carriers. For example, lactose, corn starch or derivatives thereof, talc, stearic acids or it's salts and the like can be used as carriers for tablets, coated tablets, dragées and hard gelatine capsules. Suitable carriers for soft gelatine capsules are, for example, vegetable oils, waxes, fats, semi-solid and liquid polyols and the like. However, depending on the nature of the active substance carriers may not be required for some soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical compositions can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Preferred pharmaceutical compositions comprise the following:

a) Tablet Formulation (Wet Granulation):

| Item | Ingredients | mg/tablet | | | |
|---|---|---|---|---|---|
| 1. | Compound of formula (I) | 5 | 25 | 100 | 500 |
| 2. | Lactose Anhydrous DTG (anhydrous lactose in direct tabletting grade) | 125 | 105 | 30 | 150 |
| 3. | Sta-Rx 1500 (a pre-gelatinized starch powder) | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure:
1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

b) Capsule Formulation

| Item | Ingredients | mg/capsule | | | |
|---|---|---|---|---|---|
| 1. | Compound of formula (I) | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure:
1. Mix items 1, 2 and 3 in a suitable mixer for 30 minutes.
2. Add items 4 and 5 and mix for 3 minutes.
3. Fill into a suitable capsule.

c) Micro suspension
1. Weigh 4.0 g glass beads in custom made tube GL 25, 4 cm (the beads fill half of the tube).
2. Add 50 mg compound, disperse with spatulum and vortex.
3. Add 2 ml gelatin solution (weight beads: gelatin solution=2:1) and vortex.
4. Cap and wrap in aluminium foil for light protection.
5. Prepare a counter balance for the mill.
6. Mill for 4 hours, 20/s in a Retsch mill (for some substances up to 24 hours at 30/s).
7. Extract suspension from beads with two layers of filter (100 μm) on a filter holder, coupled to a recipient vial by centrifugation at 400 g for 2 min.
8. Move extract to measuring cylinder.
9. Repeat washing with small volumes (here 1 ml steps) until final volume is reached or extract is clear.
10. Fill up to final volume with gelatin and homogenise.

The above described preparation yields micro-suspensions of the compounds of formula I-A with particle sizes between 1 and 10 μm. The suspensions are suitable for oral applications and can be used in the in vivo assay described above.

Pharmaceutical compositions containing a compound of the present invention or a pharmaceutically acceptable salt or ester thereof and a therapeutically inert carrier are also an object of the present invention, as is a process for their production, which comprises bringing one or more compounds of the present invention and/or pharmaceutically acceptable salts or esters and, if desired, one or more other therapeutically valuable substances into a galenical administration form together with one or more therapeutically inert carriers.

In accordance with the invention the compounds of the present invention as well as their pharmaceutically acceptable salts or esters are useful in the control or prevention of illnesses. Based on their HER-signalling pathway inhibition and their antiproliferative activity, said compounds are useful for the treatment of diseases such as cancer in humans or animals and for the production of corresponding pharmaceutical compositions. The dosage depends on various factors such as manner of administration, species, age and/or individual state of health.

The following examples and references are provided to aid the understanding of the present invention, the true scope of which is set forth in the appended claims. It is understood that modifications can be made in the procedures set forth without departing from the spirit of the invention.

EXAMPLES

A: Starting Materials

Preparation of 3-Chloro-6-iodo-pyridazine

To a suspension of 3,6-dichloro-pyridazine (1.0 g, 6.71 mmol) and NaI (1.35 g, 9.0 mmol) in chloroform (2.5 ml) a Hydroiodic acid (57 wt. %) (2.85 g, 25.6 mmol) is added at 0° C. The mixture is stirred for 20 hours (h) at room temperature (r.t.) and then poured into a mixture of 100 ml ice water and 20 ml 10N sodium hydroxide (NaOH). Chloroform (50 ml) is added and the mixture is stirred for 10 minutes (min). The organic phase is separated, the aqueous layer is extracted with chloroform (1×50 ml) and the combined organic phases dried over magnesium sulfate (MgSO$_4$) and concentrated in vacuo to yield 3-chloro-6-iodo-pyridazine as an off-white solid. Yield 1.16 g (72%)

MS: M=340.6 (ESI+) $^1$H-NMR (300 MHz, CDCl$_3$): 7.22 (d, J=8.9 Hz, 1H), 7.83 (d, J=8.9 Hz, 1H)

Preparation of 5-Bromo-2-chloro-pyrimidine

2-Pyrimidinol hydrochloride (13.26 g, 100 mmol) is dissolved in 2N NaOH (50 ml) and bromine (17.98 g, 112.5 mmol) is added over 15 min. The mixture is stirred for 45 min at r.t. and then concentrated in vacuo to yield a brownish solid.

The solid is suspended in phosphorus oxychloride (125 ml), N,N-dimethylaniline (9.35 g, 77 mmol) added and the mixture is heated to reflux for 3 h. After cooling the reaction mixture is poured slowly under stirring onto 1 L ice water and the resulting mixture is extracted with diethyl ether (3×200 ml). The extract is washed with brine, dried over MgSO$_4$ and concentrated in vacuo yielding 5-bromo-2-chloro-pyrimidine as a pale yellow solid. Yield 10.85 g (56%)

$^1$H-NMR (300 MHz, CDCl3): 8.70 (s, 2H)

Preparation of 5-Bromo-2-iodo-pyrimidine

To a suspension of 5-bromo-2-chloro-pyrimidine (5.80 g, 30 mmol) and sodium iodide (7.5 g, 50 mmol) in chloroform (20 ml) a Hydroiodic acid (57 wt. %) (2.85 g, 25.6 mmol) is added at 0° C. After removing the cooling the reaction mixture is stirred for 20 h at r.t. and then poured into a mixture of 200 ml ice water and 30 ml 10N NaOH. Chloroform (150 ml) is added and the mixture is stirred for 10 min. The organic phase is separated, the aqueous layer is extracted with chloroform (2×100 ml) and the combined organic phases dried over MgSO$_4$ and concentrated in vacuo to yielding 5-bromo-2-iodo-pyrimidine as a pale yellow solid. Yield 6.29 g (84%)

MS: M=284.8 (ESI+) $^1$H-NMR (300 MHz, CDCl3): 8.54 (s, 2H) 7.56(d, J=16.4 Hz, 1H), 7.59–7.66(m, 4H).

Preparation of 1-But-3-ynyl-1H-[1,2,3]triazole

But-3-yn-1-ol (49.57 g, 707.2 mmol) and triethylamine (107.7 mL, 777 mmol, dried over KOH) are dissolved in dry dichloromethane (500 mL) under a nitrogen atmosphere and cooled to 0° C. Methanesulfonyl chloride (54.8 mL, 708 mmol), dissolved in 500 mL of dry dichloromethane is added within 90 min while keeping the temperature below 5° C. The mixture is stirred for 3.5 hours at room temperature, and then poured onto 2.5 L of ice water. The organic phase is separated and washed with 2×500 mL of water and 1×250 mL of brine and dried over sodium sulfate. The volatiles are removed to yield 94.18 g of the methane sulfonate (631.2 mmol, 89.2%) as a yellow liquid.

A suspension of NaOH (37.86 g, 946.5 mmol), sodium iodide (94.65 g, 631.5 mmol) and 1H-[1,2,3]triazole (61.03 g, 883.6 mmol) in 2-methyl-2-butanol (750 mL) is refluxed for 1 h under an inert atmosphere. After cooling to room temperature the methane sulfonate (94.18 g, 631.2 mmol) is added within 5 minutes. The resulting suspension is then heated to reflux for 3 h, cooled to room temperature and concentrated in vacuo at 45° C.

Water (500 mL) and dichloro methane (1 L) are added and the organic phase is separated, dried over sodium sulfate and the volatiles removed at 30° C. The residue is distilled at 1 mm Hg. A forerun is collected at 20–70° C. The main fraction distilled at 123–129° C. as a colourless, turbid liquid. After filtration over Celite (diatomite), 1-but-3-ynyl-1H-[1,2,3]triazole is obtained as a colourless liquid (29.77 g, 38.9%).

¹H-NMR (400 MHz, CDCl₃) δ: 2.05 (t, 1H), 2.75 (dt, 2H), 4.5 (t, 2H), 7.65 (1H), 7.7 (s, 1H).

Preparation of {2-[2-(4-Trifluoromethoxy-phenyl)-vinyl]-oxazol-4-yl}-methanol A solution of 4-chloromethyl-2-[2-(4-trifluoromethoxy-phenyl)-vinyl]-oxazole (0.300 g, 0.99 mmol) and sodium acetate (0.162 g, 1.976 mmol) in acetic acid (5 ml) is refluxed for 48 h. The reaction mixture is cooled to r.t., concentrated in vacuo and the resulting residue is dissolved in ethanol (2 ml) and 5M potassium hydroxide (KOH) (5 ml). The solution is refluxed for 5 h and cooled to r.t. Saturated ammonium chloride (NH₄Cl) is added and the mixture is extracted with ethyl acetate (3×). The extract is washed with brine, dried over Na₂SO₄ and concentrated in vacuo. The crude product is purified by flash column chromatography (ethyl acetate/hexanes 1:1) yielding {2-[2-(4-Trifluoromethoxy-phenyl)-vinyl]-oxazol-4-yl}-methanol as a colorless solid. Yield 200 mg (71%).

¹H-NMR (400 MHz, CDCl₃): δ=4.64 (s, 2H, CH₂—O), 6.85 (d, 1H, =CH), 7.21 (d, 2H, Ph), 7.49–7.57 (m, 4H).

Preparation of {2-[2-(2-fluoro-4-trifluoromethyl-phenyl)-vinyl]-oxazol-4-yl}-methanol A solution of 4-chloromethyl-2-[2-(2-fluoro-4-trifluoromethyl-phenyl)-vinyl]-oxazole (1.000 g, 3.27 mmol) and sodium acetate (0.536 g, 6.54 mmol) in acetic acid (10 ml) is refluxed for 55 h. The reaction mixture is cooled to r.t., concentrated in vacuo and the resulting residue is dissolved in ethanol (5 ml) and 7M potassium hydroxide (KOH) (12 ml). The solution is refluxed for 5 h and cooled to r.t. Saturated ammonium chloride (NH₄Cl) is added and the mixture is extracted with ethyl acetate (3×). The extract is washed with brine, dried over Na₂SO₄ and concentrated in vacuo. The crude product is purified by flash column chromatography (ethyl acetate/hexanes 1:1) yielding {2-[2-(2-fluoro-4-trifluoromethyl-phenyl)-vinyl]-oxazol-4-yl}-methanol as a colorless solid. Yield 0.791 g (84%).

¹H-NMR (400 MHz, CDCl₃): δ=4.65 (s, 2H, CH₂—O), 7.09 (d, 1H, =CH), 7.36 (d, 1H, Ph), 7.42 (d, 1H, Ph), 7.61 (s, 1H, oxazole), 7.63 (d, 1H, =CH), 7.66 (dd, 1H, Ph).

Preparation of {2-[2-(4-chloro-2-fluoro-phenyl)-vinyl]-oxazol-4-yl}-methanol A solution of 2-[2-(4-chloro-2-fluoro-phenyl)-vinyl]-4-chloromethyl-oxazole (0.800 g, 2.94 mmol) and sodium acetate (0.482 g, 5.88 mmol) in acetic acid (10 ml) is refluxed for 55 h. The reaction mixture is cooled to r.t., concentrated in vacuo and the resulting residue is dissolved in ethanol (4 ml) and 5M potassium hydroxide (KOH) (15 ml). The solution is refluxed for 5 h and cooled to r.t. Saturated ammonium chloride (NH₄Cl) is added and the mixture is extracted with ethyl acetate (3×). The extract is washed with brine, dried over Na₂SO₄ and concentrated in vacuo. The crude product is purified by flash column chromatography (ethyl acetate/hexanes 1:1) yielding {2-[2-(4-chloro-2-fluoro-phenyl)-vinyl]-oxazol-4-yl}-methanol as a colorless solid. Yield 0.582 g (78%).

¹H-NMR (400 MHz, CDCl₃): δ=4.63 (s, 2H, CH₂—O), 6.95 (d, 1H, =CH), 7.11–7.15 (m, 2H, Ph), 7.47 (t, 1H, Ph), 7.57 (d, 1H, =CH), 7.58 (s, 1H, oxazole).

B. Products

Example 1

3-(4-[1,2,3]Triazol-1-yl-but-1-ynyl)-6-{2-[2-(4-trifluoromethyl-phenyl)-vinyl]-oxazol-4-ylmethoxy}-pyridazine 4-Hydroxymethyl-2-[2-(4-trifluoromethyl-phenyl)-vinyl]-oxazole (0.090 g, 0.33 mmol) is dissolved in anhydrous tetrahydrofuran (THF) (3 ml) followed by the addition of sodium tert-butoxide (NaOtBu) (0.048 g, 0.5 mmol). After stirring for 10 min at r.t. the mixture is cooled to 0° C., 3-chloro-6-iodo-pyridazine (0.060 g, 0.33 mmol) in THF (3 ml) is added slowly over a period of 15 min and stirred for further 30 min at 0° C. Ethyl acetate (30 ml) is added; the mixture is washed with saturated ammonium chloride (NH₄Cl), dried over MgSO₄ and concentrated in vacuo. After flash column chromatography (ethyl acetate/hexanes 1:2->2:3) 3-iIodo-6-{2-[2-(4-trifluoromethyl-phenyl)-vinyl]-oxazol-4-ylmethoxy}-pyridazine can be isolated as a pale yellow solid. Yield 0.12 g (77%).

MS: M=382.0 (ESI+)

¹H-NMR (300 MHz, CDCl₃): 5.50 (s, 2H), 6.76(d, J=9.1 Hz, 1H), 7.01(d, J=16.4 Hz, 1H), 7.56(d, J=16.4 Hz, 1H), 7.60–7.63(m, 4H), 7.68(d, J=9.1 Hz, 1H), 7.85(s, 1H).

3-Iodo-6-{2-[2-(4-trifluoromethyl-phenyl)-vinyl]-oxazol-4-ylmethoxy}-pyridazine (0.114 g, 0.25 mmol), 1-but-3-ynyl-1H-[1,2,3]triazole (0.040 g, 0.30 mmol) and triethyl amine (NEt₃) (0.125 ml) are dissolved in THF (1 ml) and copper iodide (CuI) (0.0048 g, 0.025 mmol) is added under stirring. After passing a stream of argon through the mixture for 10 min bis(triphenylphosphine)palladium(II) dichloride (0.088 g, 0.0125 mmol) is added and stirring is continued for 3 h at r.t. Ethyl acetate (30 ml) is added; the mixture is washed with saturated ammonium chloride (NH₄Cl) and brine, dried over MgSO₄ and concentrated in vacuo. The crude product is purified by flash column chromatography (ethyl acetate/hexanes 1:3->ethyl acetate (100%)) yielding 3-(4-[1,2,3]triazol-1-yl-but-1-ynyl)-6-{2-[2-(4-trifluoromethyl-phenyl)-vinyl]-oxazol-4-ylmethoxy}-pyridazine as a colorless solid. Yield 93 mg (64%).

MS: M=467.1 (ESI+).

Example 2

3-(4-[1,2,3]Triazol-1-yl-butyl)-6-{2-[2-(4-trifluoromethyl-phenyl)-vinyl]-oxazol-4-ylmethoxy}-pyridazine 3-(4-[1,2,3]Triazol-1-yl-but-1-ynyl)-6-{2-[2-(4-trifluoromethyl-phenyl)-vinyl]-oxazol-4-ylmethoxy}-pyridazine (0.047 g, 0.1 mmol) is dissolved in ethyl acetate (3 ml) and hydrogenated for 3 h at r.t. in the presence of palladium on charcoal (10%, 20 mg). After filtration and concentration in vacuo the residue is purified by flash column chromatography (ethyl acetate/methanol 19:1) yielding 3-(4-[1,2,3]triazol-1-yl-butyl)-6-{2-[2-(4-trifluoromethyl-phenyl)-vinyl]-oxazol-4-ylmethoxy}-pyridazine as an off-white solid.

Yield 30 mg (63%)

MS: M=471.2 (ESI+) ¹H-NMR (300 MHz, CDCl₃): 1.76–1.87 (m, 2H), 1.89–1.97 (m, 2H), 2.93 (t, J=7.4 Hz, 2H), 4.45 (t, J=7.2 Hz, 2H), 5.52 (s, 2H), 6.99(d, J=9.0 Hz, 1H), 7.02(d, J=16.4 Hz, 1H), 7.23(d, J=9.0 Hz, 1H), 7.54 (s, 1H), 7.56(d, J=16.4 Hz, 1H), 7.63(m, 4H), 7.70(s, 1H), 7.87(s, 1H).

Example 2a 3-(4-[1,2,3]Triazol-1-yl-but-1-enyl)-6-{2-[2-(4-trifluoromethyl-phenyl)-vinyl]-oxazol-4-ylmethoxy}-pyridazine 3-(4-[1,2,3]Triazol-1-yl-but-1-ynyl)-6-{2-[2-(4-trifluoromethyl-phenyl)-vinyl]-oxazol-4-ylmethoxy}-pyridazine (0.047 g, 0.1 mmol) is dissolved in ethyl acetate (3 ml) and hydrogenated for 1 h at r.t. in the presence of palladium on charcoal (10%, 5 mg). After filtration and concentration in vacuo the residue yielded 3-(4-[1,2,3]triazol-1-yl-but-1-enyl)-6-{2-[2-(4-trifluoromethyl-phenyl)-vinyl]-oxazol-4-ylmethoxy}-pyridazine as an off-white solid. The raw product contained 60% product and 40% educt. The ratio was detected by HPLC-MS (High Performance Liquid Chromatography-Mass Spectrometry; Eluent: $H_2O/CH_3CN$, Gradient: in 20 minutes from 0% (volume to volume (v/v)) to 95% (v/v) $CH_3CN$, UV-detection at 226 nm).

MS: M=469.2 (ESI+)

Example 3

5-(4-[1,2,3]Triazol-1-yl-but-1-ynyl)-2-{2-[2-(4-trifluoromethyl-phenyl)-vinyl]-oxazol-4-ylmethoxy}-pyrimidine 4-Hydroxymethyl-2-[2-(4-trifluoromethyl-phenyl)-vinyl]-oxazole (0.538 g, 2.0 mmol) is dissolved in anhydrous tetrahydrofuran (THF) (10 ml) followed by the addition of NaOtBu (0.231 g, 2.4 mmol). After stirring for 15 min at r.t., 5-bromo-2-chloro-pyrimidine (0.426 g, 2.2 mmol) in THF (5 ml) is added slowly over a period of 10 min and stirred for further 30 min at r.t. Chloroform (25 ml) is added; the mixture is washed with 0.5N hydrochloric acid (HCl) and water, dried over $MgSO_4$ and concentrated in vacuo. After flash column chromatography (100% chloroform) 5-bromo-2-{2-[2-(4-trifluoromethyl-phenyl)-vinyl]-oxazol-4-ylmethoxy}-pyrimidine can be isolated as an off-white solid. Yield 0.60 g (71%).

MS: M=426.0 (ESI+) $^1$H-NMR (300 MHz, CDCl$_3$): 5.40 (s, 2H), 7.00 (d, J=16.4 Hz, 1H), 7.54(d, J=16.4 Hz, 1H), 7.60–7.66(m, 4H), 7.74(s, 1H), 8.57(s, 2H).

To a solution of 5-bromo-2-{2-[2-(4-trifluoromethyl-phenyl)-vinyl]-oxazol-4-ylmethoxy}-pyrimidine (0.213 g, 0.50 mmol), 1-but-3-ynyl-1H-[1,2,3]triazole (0.067 g, 0.55 mmol) and diisopropyl amine (iPr$_2$NH) (2 ml) in DMF (4 ml) and THF (2 ml), copper iodide (CuI) (0.0048 g, 0.025 mmol) is added under stirring. After passing a stream of argon through the mixture for 10 min tetrakis(triphenylphosphine)palladium (0.029 g, 0.025 mmol) is added and the mixture is heated at 80° C. for 3 h. Ethyl acetate (150 ml) is added, the resulting mixture is washed with ammonium chloride (NH$_4$Cl) and brine, dried over $MgSO_4$ and concentrated in vacuo. The crude product is purified by flash column chromatography (chloroform (100%)->ethyl acetate (100%)) yielding 5-(4-[1,2,3]triazol-1-yl-but-1-ynyl)-2-{2-[2-(4-trifluoromethyl-phenyl)-vinyl]-oxazol-4-ylmethoxy}-pyrimidine as a pale yellow solid. Yield 138 mg (59%).

MS: M=467.1 (ESI+).

Example 4

5-(4-[1,2,3]Triazol-1-yl-butyl)-2-{2-[2-(4-trifluoromethyl-phenyl)-vinyl]-oxazol-4-ylmethoxy}-pyrimidine 5-(4-[1,2,3]Triazol-1-yl-but-1-ynyl)-2-{2-[2-(4-trifluoromethyl-phenyl)-vinyl]-oxazol-4-ylmethoxy}-pyrimidine (0.047 g, 0.1 mmol) is dissolved in ethyl acetate (3 ml) and hydrogenated for 1 h at r.t. in the presence of palladium on charcoal (10%, 20 mg). After filtration and concentration in vacuo the crude product is purified by flash column chromatography (ethyl acetate/hexanes 1:3->ethyl acetate (100%)) yielding 5-(4-[1,2,3]-triazol-1-yl-butyl)-2-{2-[2-(4-trifluoromethyl-phenyl)-vinyl]-oxazol-4-ylmethoxy}-pyrimidine as a white solid. Yield 35 mg (74%)

MS: M=471.0 (API+)
$^1$H-NMR (300 MHz, CDCl$_3$): 1.60–1.70 (m, 2H), 1.98–2.11 (m, 2H), 2.62 (t, J=7.4Hz, 2H), 4.46 (t, J=7.2 Hz, 2H), 5.43 (s, 2H), 7.04(d, J=16.4 Hz, 1H), 7.52–7.58(m, 2H), 7.61–7.67(m, 4H), 7.76(s, 1H), 7.79(s, 1H), 8.39(s, 2H).

Example 5

2-(4-[1,2,3]Triazol-1-yl-butyl)-5-{2-[2-(4-trifluoromethyl-phenyl)-vinyl]-oxazol-4-ylmethoxy}-pyrimidine 5-Bromo-2-iodo-pyrimidine (1.14 g, 4.0 mmol), 1-but-3-ynyl-1H-[1,2,3]triazole (0.533 g, 4.4 mmol) and triethyl amine (NEt$_3$) (2 ml) are dissolved in DMF (1 ml) and copper iodide (CuI) (0.38 g, 0.2 mmol) is added under stirring. After passing a stream of argon through the mixture for 10 min bis(triphenylphosphine) palladium(II) dichloride (0.140 g, 0.2 mmol) is added and stirring is continued for 3 h at r.t. Chloroform (300 ml) is added; the mixture is washed with 1N HCl and water, dried over $MgSO_4$ and concentrated in vacuo. The residue is purified by flash column chromatography (chloroform (100%)->ethyl acetate (100%)) yielding 5-bromo-2-(4-[1,2,3]triazol-1-yl-but-1-ynyl)-pyrimidine as a beige solid. Yield 0.96 g (86%).

MS: M=277.9 (ESI+)

5-Bromo-2-(4-[1,2,3]triazol-1-yl-but-1-ynyl)-pyrimidine (0.350 g, 1.26 mmol) is dissolved in ethyl acetate (3 ml) and hydrogenated for 2 h at r.t. in the presence of palladium on charcoal (10%, 175 mg). The reaction mixture is filtered and concentrated in vacuo to yield 5-Bromo-2-(4-[1,2,3]triazol-1-yl-butyl)-pyrimidine as a beige solid. Yield 290 mg (82%)

MS: M=281.8 (ESI+)

To a solution of tris(dibenzylideneacetone)dipalladium(0) (0.027 g, 0.03 mmol in dioxane (6 ml) tricyclohexylphosphine (0.084 g, 0.30 mmol) is added and the mixture stirred under argon for 30 min. A solution of 5-bromo-2-(4-[1,2,3]triazol-1-yl-butyl)-pyrimidine (0.282 g, 1.0 mmol), bis(pinacolato)diboron (0.279 g, 1.1 mmol) and potassium acetate (0.147 g, 1.5 mmol) is added and the mixture is heated at 80° C. for 5 h. After cooling the mixture is concentrated in vacuo and the crude product is purified by flash column chromatography (ethyl acetate (100%)->ethyl acetate/tetrahydrofuran 1:1) yielding 2-(4-[1,2,3]triazol-1-yl-butyl)-pyrimidine-5-boronic acid as a beige solid. Yield 140 mg (57%).

MS: M=248.2 (ESI+)

2-(4-[1,2,3]Triazol-1-yl-butyl)-pyrimidine-5-boronic acid (0.099 g, 0.40 mmol) is dissolved in THF (0.5 ml) and water (0.5 ml) and hydrogen peroxide (30 wt %) (0.054 g, 0.48 mmol) is added. After stirring the solution at r.t. for 2 h, brine (3 ml) is added and the mixture is extracted with THF (2×10 ml). The combined organic phases are dried over $MgSO_4$ and concentrated in vacuo yielding 2-(4-[1,2,3]triazol-1-yl-butyl)-pyrimidin-5-ol as a off-white solid. Yield 85 mg (97%).

MS: M=219.9 (ESI+)

A mixture of 4-chlormethyl-2-[2-(4-trifluoromethyl-phenyl)-vinyl]-oxazole (0.144 g, 0.50 mmol), 2-(4-[1,2,3]triazol-1-yl-butyl)-pyrimidin-5-ol (0.078 g, 0.357 mmol) and cesium carbonate (Cs$_2$CO$_3$) (0.175 g, 0.536 mmol) in DMF (10 ml) is kept at 80° C. for 2 h. After cooling ethyl acetate (25 ml) is added, the mixture is washed with sat. NH$_4$Cl and brine, dried over MgSO$_4$ and concentrated in vacuo. The crude product is purified by flash column chromatography (ethyl acetate (100%)->ethyl acetate/methanol 9:1) and 2-(4-[1,2,3]-triazol-1-yl-butyl)-5-{2-[2-(4-trifluoromethyl-phenyl)-vinyl]-oxazol-4-ylmethoxy}-pyrimidine can be isolated as a white solid. Yield 40 mg (24%).

MS: M=471.1 (ESI+) $^1$H-NMR (300 MHz, CDCl$_3$): 1.82–1.92 (m, 2H), 1.97–2.06 (m, 2H), 2.99 (t, J=7.2 Hz, 2H), 4.45 (t, J=7.2 Hz, 2H), 5.12 (s, 2H), 7.02(d, J=16.4 Hz, 1H), 7.56–7.62(m, 2H), 7.65–7.69(m, 4H), 7.71(s, 1H), 7.76(s, 1H), 8.47(s, 2H).

Example 6

2-(4-[1,2,3]Triazol-1-yl-but-1-ynyl)-5-{2-[2-(4-trifluoromethyl-phenyl)-vinyl]-oxazol-4-ylmethoxy}-pyrazine A mixture of 4-chlormethyl-2-[2-(4-trifluoromethyl-phenyl)-vinyl]-oxazole (0.345 g, 1.2 mmol), 5-bromo-pyrazin-2-ol (0.175 g, 1.0 mmol) and cesium carbonate (Cs$_2$CO$_3$) (0.489 g, 1.5 mmol) in DMF (4 ml) is kept at 80° C. for 1 h. After cooling ethyl acetate (40 ml) is added, the mixture is washed with sat. NH$_4$Cl and brine, dried over MgSO$_4$ and concentrated in vacuo. The crude product is purified by flash column chromatography (ethyl acetate/hexane 1:9->ethyl acetate/hexane 1:2) yielding 2-bromo-5-{2-[2-(4-trifluoromethyl-phenyl)-vinyl]-oxazol-4-yl-methoxy}-pyrazine as a white solid. Yield 122 mg (29%).

MS: M=425.9 (ESI+) $^1$H-NMR (300 MHz, CDCl$_3$): 5.34 (s, 2H), 7.01(d, J=16.4 Hz, 1H), 7.57(d, J=16.4 Hz, 1H), 7.60–7.63(m, 4H), 7.73 (s, 1H), 8.09(d, J=1.2 Hz, 1H), 8.21(d, J=1.2 Hz, 1H).

2-Bromo-5-{2-[2-(4-trifluoromethyl-phenyl)-vinyl]-oxazol-4-ylmethoxy}-pyrazine (0.128 g, 0.30 mmol), 1-but-3-ynyl-1H-[1,2,3]triazole (0.044 g, 0.36 mmol) and triethyl amine (NEt$_3$) (0.60 ml) are dissolved in THF (1.5 ml) and DMF (1.5 ml), and copper iodide (CuI) (0.006 g, 0.03 mmol) is added under stirring. After passing a stream of argon through the mixture for 10 min tetrakis(triphenylphosphine)palladium (0.017 g, 0.015 mmol) is added and the mixture is heated at 80° C. for 1.5 h. After cooling ethyl acetate (40 ml) is added, the mixture is washed with saturated HCl and brine, dried over MgSO$_4$ and concentrated in vacuo. The crude product is purified by flash column chromatography (ethyl acetate/hexanes 1:1->ethyl acetate (100%)) yielding 2-(4-[1,2,3]triazol-1-yl-but-1-ynyl)-5-{2-[2-(4-trifluoromethyl-phenyl)-vinyl]-oxazol-4-ylmethoxy}-pyrazine as a pale yellow solid. Yield 134 mg (96%).

MS: M=467.1 (ESI+) $^1$H-NMR (300 MHz, CDCl$_3$): 3.09 (t, J=7.2 Hz, 2H), 4.47 (t, J=7.2 Hz, 2H), 5.36 (s,2H), 7.01(d, J=16.4 Hz, 1H), 7.57(d, J=16.4 Hz, 1H), 7.63–7.68(m, 4H), 7.74–7.77(m, 3H), 8.16(s, 1H), 8.23(s, 1H).

Example 7

2-(4-[1,2,3]Triazol-1-yl-butyl)-5-{2-[2-(4-trifluoromethyl-phenyl)-vinyl]-oxazol-4-ylmethoxy}-pyrazine 2-(4-[1,2,3]Triazol-1-yl-but-1-ynyl)-5-{2-[2-(4-trifluoromethyl-phenyl)-vinyl]-oxazol-4-ylmethoxy}-pyrazine (0.060 g, 0.129 mmol) is dissolved in ethyl acetate (30 ml) and hydrogenated for 30 min at r.t. in the presence of palladium on charcoal (10%, 30 mg). After filtration and concentration in vacuo the residue is purified by preparative HPLC yielding 3-(4-[1,2,3]triazol-1-yl-butyl)-6-{2-[2-(4-trifluoromethyl-phenyl)-vinyl]-oxazol-4-ylmethoxy}-pyridazine as an off-white solid. Yield 38 mg (63%)

MS: M=471.1 (ESI+) $^1$H-NMR (300 MHz, CDCl$_3$): 1.71–1.81 (m, 2H), 1.98–2.06 (m, 2H), 2.80 (t, J=7.2 Hz, 2H), 4.45 (t, J=7.2 Hz, 2H), 5.36 (s, 2H), 7.05(d, J=16.4 Hz, 1H), 7.54–7.60 (m, 2H), 7.64–7.67(m, 4H), 7.73(s, 1H), 7.80 (s, 1H), 7.98(d, J=1.1 Hz, 1H), 8.23(d, J=1.1 Hz, 1H).

Example 8

5-(4-[1,2,3]Triazol-1-yl-butyl)-2-{2-[2-(4-trifluoromethoxy-phenyl)-vinyl]-oxazol-4-ylmethoxy}-pyrimidine 5-Bromo-2-chloro-pyrimidine (0.500 g, 2.53 mmol), 1-but-3-ynyl-1H-[1,2,3]triazole (0.368 g, 3.03 mmol) and triethyl amine (NEt$_3$) (5.0 ml) are dissolved in DMF (10 ml) and copper iodide (CuI) (0.052 g, 0.27 mmol) is added under stirring. After passing a stream of argon through the mixture for 10 min tetrakis(triphenylphosphine)palladium(0) (0.149 g, 0.13 mmol) is added and stirring is continued for 4 h at 80° C. Dichloromethane (125 ml) is added, the mixture is washed with 0.5N hydrochloric acid (HCl) and brine, dried over Na$_2$SO$_4$ and concentrated in vacuo. The crude product is purified by flash column chromatography (ethyl acetate/hexanes 4:1) yielding 2-chloro-5-(4-[1,2,3]triazol-1-yl-but-1-ynyl)-pyrimidine as a colorless solid. Yield 373 mg (63%).

MS: M=234 (API+) $^1$H NMR (400 MHz, CDCl$_3$): δ=3.10 (t, 2H, CH$_2$—C≡), 4.63 (t, 2H, CH$_2$-N), 7.64 (s, 1H, triazole), 7.72 (s, 1H, triazole) 8.54 (s, 2H, pyrimidine).

2-Chloro-5-(4-[1,2,3]triazol-1-yl-but-1-ynyl)-pyrimidine (2.52 g, 10.8 mmol) is dissolved in ethyl acetate (210 ml) and hydrogenated for 2.5 h at r.t. in the presence of palladium on calcium carbonate (10%, 2.55 g). The reaction mixture is filtered and concentrated in vacuo to yield 2-chloro-5-(4-[1,2,3]triazol-1-yl-butyl)-pyrimidine as a colorless solid. Yield 2.15 g (84%)

MS: M=236.2, 238.2 (ESI+) $^1$H-NMR (400 MHz, CDCl$_3$): δ=1.60–1.68 (m, 2H, CH$_2$—CH$_2$—C≡), 1.94–2.02 (m, 2H, CH$_2$—CH$_2$—N), 2.62 (t, 2H, CH$_2$—C≡), 4.42 (t, 2H, CH$_2$—N), 7.50 (s, 1H, triazole), 7.70 (s, 1H, triazole), 8.41 (s, 2H, pyrimidine).

{2-[2-(4-Trifluoromethoxy-phenyl)-vinyl]-oxazol-4-yl}-methanol (0.097 g, 0.34 mmol) is dissolved in anhydrous tetrahydrofuran (THF) (4 ml) followed by addition of sodium tert-butoxide (NaOtBu) (0.040 g, 0.41 mmol). After stirring for 15 min at r.t. 2-chloro-5-(4-[1,2,3]triazol-1-yl-butyl)-pyrimidine (0.090 g, 0.38 mmol) is added slowly and stirred for further 1.5 h at r.t. Ethyl acetate (20 ml) is added; the mixture is washed with saturated ammonium chloride (NH$_4$Cl), dried over MgSO$_4$ and concentrated in vacuo. After flash column chromatography (ethyl acetate) 5-(4-[1,2,3]triazol-1-yl-butyl)-2-{2-[2-(4-trifluoromethoxy-phenyl)-vinyl]-oxazol-4-ylmethoxy}-pyrimidine is obtained as a colorless solid. Yield 0.104 g (63%).

MS: M=487.5 (ESI+) $^1$H-NMR (400 MHz, CDCl$_3$): δ=1.58–1.65 (m, 2H, CH$_2$—CH$_2$—C≡), 1.93–2.00 (m, 2H, CH$_2$—CH$_2$—N), 2.57 (t, 2H, CH$_2$—CH$_2$—C≡), 4.41 (t, 2H, CH$_2$—N), 5.37 (s, 2H, CH$_2$—O), 6.88 (d, 1H, =CH), 7.21 (d, 2H, Ph), 7.48 (d, 1H, =CH), 7.50–7.53 (m, 3H), 7.69–7.71 (m, 2H), 8.32 (s, 2H, pyrimidine).

Example 9

2-{2-[2-(2-Fluoro-4-trifluoromethyl-phenyl)-vinyl]-oxazol-4-ylmethoxy}-5-(4-[1,2,3]triazol-1-yl-butyl)-pyrimidine {2-[2-(2-Fluoro-4-trifluoromethyl-phenyl)-vinyl]-oxazol-4-yl}-methanol (0.100 g, 0.35 mmol) is dissolved in anhydrous tetrahydrofuran (THF) (3 ml) followed by the addition of sodium tert-butoxide (NaOtBu) (0.041 g, 0.42 mmol). After stirring for 15 min at r.t. 2-chloro-5-(4-[1,2,3]triazol-1-yl-butyl)-pyrimidine (0.075 g, 0.32 mmol) is added slowly and stirred for further 3 h at r.t. Ethyl acetate (20 ml) is added, the mixture is washed with saturated ammonium chloride ($NH_4Cl$), dried over $MgSO_4$ and concentrated in vacuo. After flash column chromatography (ethyl acetate/methanol 97:3) 2-{2-[2-(2-fluoro-4-trifluoromethyl-phenyl)-vinyl]-oxazol-4-ylmethoxy}-5-(4-[1,2,3]triazol-1-yl-butyl)-pyrimidine is obtained as a colorless solid. Yield 0.104 g (75%).

MS: M=489.2 (ESI+) $^1$H-NMR (400 MHz, $CDCl_3$): δ=1.58–1.65 (m, 2H, $CH_2$—$CH_2$—C=), 1.93–2.02 (m, 2H, $CH_2$—$CH_2$—N), 2.58 (t, 2H, $CH_2$—$CH_2$—C=), 4.42 (t, 2H, $CH_2$—N), 5.39 (s, 2H, $CH_2$—O), 7.07 (d, 1H, =CH), 7.35 (d, 1H, Ph), 7.41 (d, 1H, Ph), 7.51 (s, 1H, triazole), 7.61 (d, 1H, =CH), 7.65 (dd, 1H, Ph), 7.71 (s, 1H), 7.74 (s, 1H), 8.33 (s, 2H, pyrimidine).

Example 10

2-{2-[2-(4-Chloro-2-fluoro-phenyl)-vinyl]-oxazol-4-ylmethoxy}-5-(4-[1,2,3]triazol-1-yl-butyl)-pyrimidine {2-[2-(4-Chloro-2-fluoro-phenyl)-vinyl]-oxazol-4-yl}-methanol (0.100 g, 0.39 mmol) is dissolved in anhydrous tetrahydrofuran (THF) (3 ml) followed by addition of sodium tert-butoxide (NaOtBu) (0.046 g, 0.47 mmol). After stirring for 15 min at r.t. 2-chloro-5-(4-[1,2,3]triazol-1-yl-butyl)-pyrimidine (0.085 g, 0.36 mmol) is added slowly and stirred for further 3 h at r.t. Ethyl acetate (20 ml) is added, the mixture is washed with saturated ammonium chloride ($NH_4Cl$), dried over $MgSO_4$ and concentrated in vacuo. After flash column chromatography (ethyl acetate/methanol 98:2) 2-{2-[2-(4-chloro-2-fluoro-phenyl)-vinyl]-oxazol-4-ylmethoxy}-5-(4-[1,2,3]triazol-1-yl-butyl)-pyrimidine is obtained as a colorless solid. Yield 0.125 g (77%).

MS: M=455.2, 457.2 (ESI+) $^1$H-NMR (400 MHz, $CDCl_3$): δ=1.60–1.66 (m, 2H, $CH_2$—$CH_2$—C=), 1.95–2.02 (m, 2H, $CH_2$—$CH_2$—N), 2.59 (t, 2H, $CH_2$—$CH_2$—C=), 4.44 (t, 2H, $CH_2$—N), 5.40 (s, 2H, $CH_2$—O), 7.02 (d, 1H, =CH), 7.12–7.18 (m, 2H, Ph), 7.46 (t, 1H, Ph), 7.53 (s, 1H, triazole), 7.57 (d, 1H, =CH), 7.72–7.74 (m, 2H, triazole, oxazole), 8.35 (s, 2H, pyrimidine).

Example 11

3-(4-[1,2,3]Triazol-1-yl-butyl)-6-{2-[2-(4-trifluoromethoxy-phenyl)-vinyl]-oxazol-4-ylmethoxy}-pyridazine 3-Chloro-6-iodo-pyridazine (11.56 g, 48.1 mmol), 1-but-3-ynyl-1H-[1,2,3]triazole (6.99 g, 57.7 mmol) and triethyl amine ($NEt_3$) (94 ml) are dissolved in DMF (188 ml) and copper iodide (CuI) (0.981 g, 5.15 mmol) is added under stirring. After passing a stream of argon through the mixture for 10 min tetrakis(triphenylphosphine)palladium(0) (2.836 g, 2.43 mmol) is added and stirring is continued for 6 h at r.t. Dichloromethane (300 ml) is added, the mixture is washed with 0.5N hydrochloric acid (HCl) and brine, dried over $Na_2SO_4$ and concentrated in vacuo. The crude product is purified by flash column chromatography (ethyl acetate) yielding 3-chloro-6-(4-[1,2,3]triazol-1-yl-but-1-ynyl)-pyridazine as a colorless solid. Yield 9.52 g (85%).

$^1$H-NMR (400 MHz, $CDCl_3$): δ=3.12 (t, 2H, $CH_2$—C=), 4.67 (t, 2H, $CH_2$—N), 7.39 (d, 1H, pyridazine), 7.45 (d, 1H, pyridazine), 7.70 (s, 1H, triazole), 7.73 (s, 1H, triazole).

3-Chloro-6-(4-[1,2,3]triazol-1-yl-but-1-ynyl)-pyridazine (2.50 g, 10.7 mmol) is dissolved in ethyl acetate (450 ml) and hydrogenated for 3.5 h at r.t. in the presence of palladium on charcoal (10%, 2.50 g). The reaction mixture is filtered and concentrated in vacuo. The residue was dissolved in THF (10 ml) and added to a solution of benzyl alcohol (0.94 ml, 9.0 mmol) and sodium tert-butoxide (NaOtBu) (0.842 g, 8.76 mmol) in THF (80 ml). After stirring for 2 h ethyl acetate (100 ml) is added, the mixture is washed with saturated ammonium chloride ($NH_4Cl$), dried over $Na_2SO_4$ and concentrated in vacuo. After flash column chromatography (ethyl acetate) 3-chloro-6-(4-[1,2,3]triazol-1-yl-butyl)-pyridazine is obtained as a colorless solid. Yield 1.14 g (45%).

$^1$H-NMR (400 MHz, $CDCl_3$): δ=1.76–1.84 (m, 2H, $CH_2$—$CH_2$—C=), 1.97–2.05 (m, 2H, $CH_2$—$CH_2$—N), 2.98 (t, 2H, $CH_2$—C=), 4.43 (t, 2H, $CH_2$—N), 7.25 (d, 1H, pyridazine), 7.40 (d, 1H, pyridazine), 7.52 (s, 1H, triazole), 7.68 (s, 1H, triazole).

{2-[2-(4-Trifluoromethoxy-phenyl)-vinyl]-oxazol-4-yl}-methanol (0.050 g, 0.17 mmol) is dissolved in anhydrous tetrahydrofuran (THF) (2 ml) followed by addition of sodium tert-butoxide (NaOtBu) (0.019 g, 0.19 mmol). After stirring for 15 min at r.t. 3-chloro-6-(4-[1,2,3]triazol-1-yl-butyl)-pyridazine (0.035 g, 0.15 mmol) is added slowly and stirred for further 4 h at 60° C. Ethyl acetate (20 ml) is added, the mixture is washed with saturated ammonium chloride ($NH_4Cl$), dried over $Na_2SO_4$ and concentrated in vacuo. After flash column chromatography (ethyl acetate/methanol 97:3) 3-(4-[1,2,3]triazol-1-yl-butyl)-6-{2-[2-(4-trifluoromethoxy-phenyl)-vinyl]-oxazol-4-ylmethoxy}-pyridazine is isolated as a colorless solid. Yield 0.049 g (69%).

MS: M=487.5 (ESI+) $^1$H-NMR (400 MHz, $CDCl_3$): δ=1.76–1.84 (m, 2H, $CH_2$—$CH_2$—C=), 1.98–205 (m, 2H, $CH_2$—$CH_2$—N), 2.96 (t, 2H, $CH_2$—$CH_2$—C=), 4.44 (t, 2H, $CH_2$—N), 5.49 (s, 2H, $CH_2$—O), 6.89 (d, 1H, =CH), 7.02 (d, 1H, pyridazine), 7.20–7.26 (m, 3H), 7.48–7.54 (m, 4H), 7.68 (s, 1H), 7.76 (s, 1H).

Example 12

3-{2-[2-(2-Fluoro-4-trifluoromethyl-phenyl)-vinyl]-oxazol-4-ylmethoxy}-6-(4-[1,2,3]triazol-1-yl-butyl)-pyridazine {2-[2-(2-Fluoro-4-trifluoromethyl-phenyl)-vinyl]-oxazol-4-yl}-methanol (0.114 g, 0.40 mmol) is dissolved in anhydrous tetrahydrofuran (THF) (3 ml) followed by the addition of sodium tert-butoxide (NaOtBu) (0.043 g, 0.43 mmol). After stirring for 15 min at r.t. 3-chloro-6-(4-[1,2,3]triazol-1-yl-butyl)-pyridazine (0.075 g, 0.32 mmol) is added slowly and stirred for further 4 h at 60° C. Ethyl acetate (20 ml) is added; the mixture is washed with saturated ammonium chloride ($NH_4Cl$), dried over $MgSO_4$ and concentrated in vacuo. After flash column chromatography (ethyl acetate/methanol 98:2) 3-{2-[2-(2-fluoro-4-trifluoromethyl-phenyl)-vinyl]-oxazol-4-ylmethoxy}-6-(4-[1,2,3]triazol-1-yl-butyl)-pyridazine is obtained as a colorless solid. Yield 0.115 g (75%).

MS: M=489.1 (ESI+) $^1$H-NMR (400 MHz, $CDCl_3$): δ=1.76–1.84 (m, 2H, $CH_2$—$CH_2$—C=), 1.98–2.08 (m, 2H, $CH_2$—$CH_2$—N), 2.95 (t, 2H, $CH_2$—$CH_2$—C=), 4.44 (t,

2H, CH₂—N), 5.50 (s, 2H, CH₂—O), 6.99 (d, 1H, pyridazine), 7.11 (d, 1H, =CH), 7.24 (d, 1H, pyridazine), 7.36 (d, 1H, Ph), 7.42 (d, 1H, Ph), 7.53 (s, 1H, triazole), 7.63 (d, 1H, =CH), 7.64 (dd, 1H, Ph), 7.68 (s, 1H), 7.80 (s, 1H).

Example 13

3-{2-[2-(4-Chloro-2-fluoro-phenyl)-vinyl]-oxazol-4-ylmethoxy}-6-(4-[1,2,3]triazol-1-yl-butyl)-pyridazine {2-[2-(4-Chloro-2-fluoro-phenyl)-vinyl]-oxazol-4-yl}-methanol (0.100 g, 0.40 mmol) is dissolved in anhydrous tetrahydrofuran (THF) (3 ml) followed by addition of sodium tert-butoxide (NaOtBu) (0.043 g, 0.43 mmol). After stirring for 15 min at r.t. 3-chloro-6-(4-[1,2,3]triazol-1-yl-butyl)-pyridazine (0.075 g, 0.32 mmol) is added slowly and stirred for further 4 h at 60° C. Ethyl acetate (20 ml) is added, the mixture is washed with saturated ammonium chloride (NH₄Cl), dried over MgSO₄ and concentrated in vacuo. After flash column chromatography (ethyl acetate/methanol 98:2) 3-{2-[2-(4-chloro-2-fluoro-phenyl)-vinyl]-oxazol-4-ylmethoxy}-6-(4-[1,2,3]triazol-1-yl-butyl)-pyridazine is isolated as a colorless solid. Yield 0.105 g (73%).

MS: M=455.02, 457.01 (ESI+) ¹H-NMR (400 MHz, CDCl₃): δ=1.76–1.84 (m, 2H, CH₂—CH₂—C=), 1.97–2.04 (m, 2H, CH₂—CH₂—N), 2.93 (t, 2H, CH₂—CH₂—C=), 4.43 (t, 2H, CH₂—N), 5.49 (s, 2H, CH₂—O), 6.98 (d, 1H, pyridazine), 7.00 (d, 1H, =CH), 7.11–7.15 (m, 2H, Ph), 7.21 (d, 1H, pyridazine), 7.43 (t, 1H, Ph), 7.53 (s, 1H, triazole), 7.56 (d, 1H, =CH), 7.68 (s, 1H), 7.77 (s, 1H).

Example 14

2-(4-[1,2,3]Triazol-1-yl-butyl)-5-{2-[2-(4-trifluoromethoxy-phenyl)-vinyl]-oxazol-4-ylmethoxy}-pyrazine 2-Bromo-5-iodo-pyrazine (13.69 g, 48.0 mmol), 1-but-3-ynyl-1H-[1,2,3]triazole (7.01 g, 57.9 mmol) and triethyl amine (NEt₃) (94 ml) are dissolved in DMF (188 ml) and copper iodide (CuI) (0.984 g, 5.17 mmol) is added under stirring. After passing a stream of argon through the mixture for 10 min tetrakis(triphenylphosphine)palladium(0) (2.844 g, 2.46 mmol) is added and stirring is continued for 5 h at r.t. Dichloromethane (300 ml) is added; the mixture is washed with 0.5N hydrochloric acid (HCl) and brine, dried over Na₂SO₄ and concentrated in vacuo. The crude product is purified by flash column chromatography (ethyl acetate/hexanes 7:3) yielding 2-bromo-5-(4-[1,2,3]triazol-1-yl-but-1-ynyl)-pyrazine as a colorless solid. Yield 9.99 g (75%).

¹H-NMR (400 MHz, CDCl₃): δ=3.10 (t, 2H, CH₂—C=), 4.66 (t, 2H, CH₂—N), 7.70 (s, 1H, triazole), 7.72 (s, 1H, triazole), 8.31 (d, 1H, pyrazine), 8.60 (d, 1H, pyrazine).

2-Bromo-5-(4-[1,2,3]triazol-1-yl-but-1-ynyl)-pyrazine (2.50 g, 9.0 mmol) is dissolved in methanol (700 ml) and hydrogenated for 2 h at r.t. in the presence of platinum(IV) oxide xH₂O (0.840 g, 3.40 mmol). The reaction mixture is filtered and concentrated in vacuo to yield 2-bromo-5-(4-[1,2,3]triazol-1-yl-butyl)-pyrazine as a colorless solid. Yield 1.63 g (64%)

MS: M=282.1, 284.2 (ESI+) ¹H-NMR (400 MHz, CDCl₃): δ=1.72–1.80 (m, 2H, CH₂—CH₂—C=), 1.94–201 (m, 2H, CH₂—CH₂—N), 2.79 (t, 2H, CH₂—C=), 4.42 (t, 2H, CH₂—N), 7.51 (s, 1H, triazole), 7.69 (s, 1H, triazole), 8.17 (d, 1H, pyrazine), 8.57 (d, 1H, pyrazine).

{2-[2-(4-Trifluoromethoxy-phenyl)-vinyl]-oxazol-4-yl}-methanol (0.067 g, 0.23 mmol) is dissolved in anhydrous tetrahydrofuran (THF) (3 ml) followed by addition of sodium tert-butoxide (NaOtBu) (0.025 g, 0.25 mmol). After stirring for 15 min at r.t. 2-bromo-5-(4-[1,2,3]triazol-1-yl-butyl)-pyrazine (0.055 g, 0.19 mmol) is added slowly and stirred for further 4 h at 60° C. Ethyl acetate (20 ml) is added; the mixture is washed with saturated ammonium chloride (NH₄Cl), dried over MgSO₄ and concentrated in vacuo. After flash column chromatography (ethyl acetate/methanol 98:2) 3-{2-[2-(2-fluoro-4-trifluoromethyl-phenyl)-vinyl]-oxazol-4-ylmethoxy}-6-(4-[1,2,3]triazol-1-yl-butyl)-pyridazine is obtained as a colorless solid. Yield 0.079 g (83%).

MS: M=487.4 (ESI+) ¹H-NMR (400 MHz, CDCl₃): δ=1.71–1.78 (m, 2H, CH₂—CH₂—C=), 1.93–2.01 (m, 2H, CH₂—CH₂—N), 2.76 (t, 2H, CH₂—CH₂—C=), 4.41 (t, 2H, CH₂—N), 5.31 (s, 2H, CH₂—O), 6.89 (d, 1H, =CH), 7.21 (d, 2H, Ph), 7.50 (d, 1H, =CH), 7.51–7.53 (m, 3H), 7.68–7.70 (m, 2H), 7.92 (s, 1H), 8.20 (s, 1H, pyrazine).

Unless stated to the contrary, all compounds in the examples were prepared and characterized as described. All ranges recited herein encompass all combinations and sub-combinations included within that range limit. All patents and publications cited herein are hereby incorporated by reference in their entirety.

The invention claimed is:

1. A compound of formula (I) or pharmaceutically acceptable salts or esters thereof wherein formula I is:

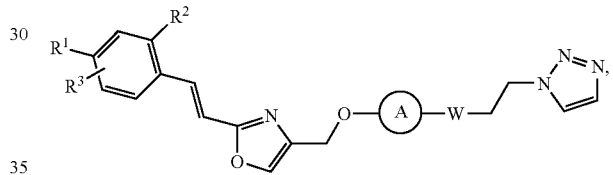

formula (I)

wherein:
(a) (1) $R^3$ is hydrogen and $R^1$ is selected from the group consisting of:
  (A) halogen;
  (B) —O-alkyl, wherein the alkyl group is optionally substituted with one or more halogens;
  (C) —S-alkyl, wherein the alkyl group is optionally substituted with one or more halogens;
  (D) —S(O)-alkyl, wherein the alkyl group is optionally substituted with one or more halogens;
  (E) —S(O)₂-alkyl, wherein the alkyl group is optionally substituted with one or more halogens;
  (F) —SF₅;
  (G) —NH-alkyl, wherein the alkyl group is optionally substituted with one or more halogens; and
  (H) alkyl, wherein the alkyl group is optionally substituted with one or more halogens; or alternatively,
(2) $R^1$ and $R^3$ are adjacent and together with the carbon atoms of the phenyl ring to which they are attached form a 5 or 6 membered heterocyclic ring;
(b) $R^2$ is selected from the group consisting of:
  (1) hydrogen; and
  (2) halogen;
(c) A is selected from the group consisting of:

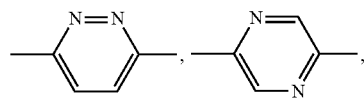

-continued

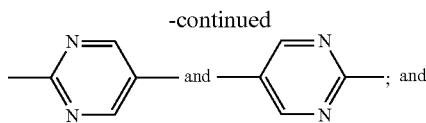

(d) W is selected from the group consisting of:
(1) —CH₂—CH₂—;
(2) —CH=CH—;
(3) —C≡C—.

2. A compound according to claim 1, wherein:
(a) R¹ is selected from the group consisting of:
(1) fluorine;
(2) chlorine;
(3) —SF₅;
(4) —O—CF₃;
(5) —OCHF₂;
(6) —S(O)—CF₃;
(7) —S(O)₂—CF₃;
(8) —S—CF₃; and
(9) —CF₃;
(b) R² is selected from the group consisting of:
(1) hydrogen;
(2) fluorine; and
(3) chlorine; and
(c) R³ is hydrogen.

3. A compound according to claim 1, wherein R¹ and R³ are adjacent and together with the phenyl ring to which they are attached form a 2,2-Difluoro-benzo[1,3]dioxolyl moiety, and R² is hydrogen.

4. A compound according to claim 1, wherein A is:

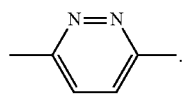

5. A compound selected from the group consisting of:
(a) 3-(4-[1,2,3]Triazol-1-yl-but-1-ynyl)-6-{2-[2-(4-trifluoromethyl-phenyl)-vinyl]-oxazol-4-ylmethoxy}-pyridazine;
(b) 3-(4-[1,2,3]Triazol-1-yl-butyl)-6-{2-[2-(4-trifluoromethyl-phenyl)-vinyl]-oxazol-4-ylmethoxy}-pyridazine;
(c) 3-(4-[1,2,3]Triazol-1-yl-butyl)-6-{2-[(E)-2-(4-trifluoromethoxy-phenyl)-vinyl]-oxazol-4-ylmethoxy}-pyridazine;
(d) 3-{2-[(E)-2-(2-Fluoro-4-trifluoromethyl-phenyl)-vinyl]-oxazol-4-ylmethoxy}-6-(4-[1,2,3]triazol-1-yl-butyl)-pyridazine; and
(e) 3-{2-[(E)-2-(4-Chloro-2-fluoro-phenyl)-vinyl]-oxazol-4-ylmethoxy}-6-(4-[1,2,3]triazol-1-yl-butyl)-pyridazine.

6. A compound according to claim 1, wherein A is:

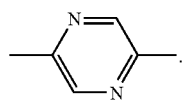

7. A compound according to claim 6 selected from the group consisting of:
(a) 2-(4-[1,2,3]Triazol-1-yl-but-1-ynyl)-5-{2-[2-(4-trifluoromethyl-phenyl)vinyl]-oxazol-4-ylmethoxy}-pyrazine;
(b) 2-(4-[1,2,3]Triazol-1-yl-butyl)-5-{2-[2-(4-trifluoromethyl-phenyl)-vinyl]-oxazol-4-ylmethoxy}-pyrazine; and
(c) 2-(4-[1,2,3]Triazol-1-yl-butyl)-5-{2-[(E)-2-(4-trifluoromethoxy-phenyl)-vinyl]-oxazol-4-ylmethoxy}-pyrazine.

8. A compound according to claim 1, wherein A is:

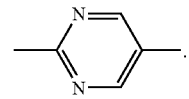

9. The compounds according to claim 8 selected from the group consisting of:
(a) 5-(4-[1,2,3]Triazol-1-yl-but-1-ynyl)-2-{2-[2-(4-trifluoromethyl-phenyl)-vinyl]-oxazol-4-ylmethoxy}-pyrimidine;
(b) 5-(4-[1,2,3]Triazol-1-yl-butyl)-2-{2-[2-(4-trifluoromethyl-phenyl)-vinyl]-oxazol-4-ylmethoxy}-pyrimidine;
(c) 5-(4-[1,2,3]Triazol-1-yl-butyl)-2-{2-[(E)-2-(4-trifluoromethoxy-phenyl)-vinyl]-oxazol-4-ylmethoxy}-pyrimidine;
(d) 2-{2-[(E)-2-(2-Fluoro-4-trifluoromethyl-phenyl)-vinyl]-oxazol-4-ylmethoxy}-5-(4-[1,2,3]triazol-1-yl-butyl)-pyrimidine; and
(e) 2-{2-[(E)-2-(4-Chloro-2-fluoro-phenyl)-vinyl]-oxazol-4-ylmethoxy}-5-(4-[1,2,3]triazol-1-yl-butyl)-pyrimidine.

10. A compound according to claim 1, wherein A is:

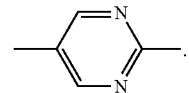

11. A compound according to claim 10 which is:
2-(4-[1,2,3]Triazol-1-yl-butyl)-5-{2-[2-(4-trifluoromethyl-phenyl)-vinyl]-oxazol-4-ylmethoxy}-pyrimidine.

12. The process for the manufacture of the compounds according to claim 1, wherein:
(a) the compound of formula (XII)

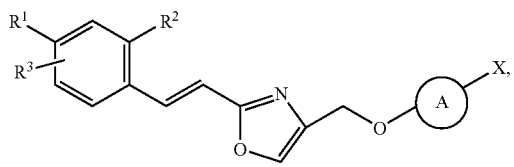

formula (XII)

wherein A is

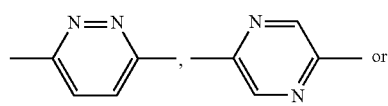

-continued

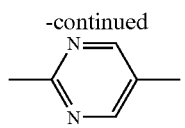

X is bromine or iodine;
and $R^1$, $R^2$ and $R^3$ are the same as defined in claim 1;
is reacted with But-3-ynyl-1H-[1,2,3]triazole, which is:

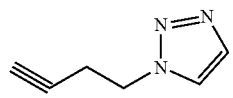

to give the corresponding compound of formula (I) wherein W is —C≡C—;

(b) the compound of formula (I) (wherein W is —C≡C—) obtained in (a), is optionally further reacted in an reductive step to give the corresponding compound of formula (I) wherein W is —CH$_2$—CH$_2$— or —CH=CH—;

(c) said compound of formula (I) is isolated from the reaction mixture; and (d) said compound of formula (I) is optionally converted into a pharmaceutically acceptable salt.

13. A pharmaceutical composition comprising, a therapeutically effective amount of a compound of formula I and a pharmaceutically acceptable vehicle, wherein formula I is:

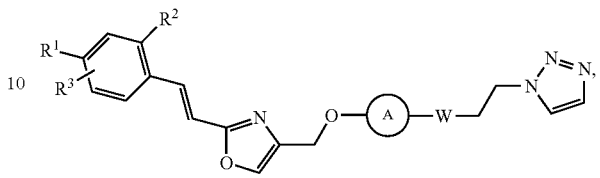

formula (I)

wherein:
(a) (1) $R^3$ is hydrogen and $R^1$ is selected from the group consisting of:
(A) halogen;
(B) —O-alkyl, wherein the alkyl group is optionally substituted with one or more halogens;
(C) —S-alkyl, wherein the alkyl group is optionally substituted with one or more halogens;
(D) —S(O)-alkyl, wherein the alkyl group is optionally substituted with one or more halogens.

* * * * *

UNITED STATES PATENT AND TRADEMARK OFFICE
CERTIFICATE OF CORRECTION

PATENT NO.        : 7,179,812 B2                                         Page 1 of 1
APPLICATION NO. : 11/096286
DATED             : February 20, 2007
INVENTOR(S)       : Bossenmaier et al.

It is certified that error appears in the above-identified patent and that said Letters Patent is hereby corrected as shown below:

Title Page, After (22) insert -- (30) Foreign Application Priority Data: "April 2, 2004 (EP) ............... 04008130.9 --

Signed and Sealed this

Twenty-eighth Day of August, 2007

JON W. DUDAS
*Director of the United States Patent and Trademark Office*